(12) United States Patent
Smith, III et al.

(10) Patent No.: US 7,700,783 B2
(45) Date of Patent: Apr. 20, 2010

(54) SYNTHESIS OF DISCODERMOLIDE AND VARIANTS THEREOF

(75) Inventors: Amos B Smith, III, Merion, PA (US); Brian Scott Freeze, Arlington, MA (US); Ming Xian, Pullman, WA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 579 days.

(21) Appl. No.: 10/575,136

(22) PCT Filed: Oct. 12, 2004

(86) PCT No.: PCT/US2004/033473

§ 371 (c)(1), (2), (4) Date: May 9, 2007

(87) PCT Pub. No.: WO2005/035489

PCT Pub. Date: Apr. 21, 2005

(65) Prior Publication Data

US 2007/0276144 A1    Nov. 29, 2007

Related U.S. Application Data

(60) Provisional application No. 60/510,097, filed on Oct. 9, 2003.

(51) Int. Cl.
- *C07D 263/00* (2006.01)
- *C07D 315/00* (2006.01)
- *C07B 41/00* (2006.01)

(52) U.S. Cl. .................. 548/230; 549/417; 568/950

(58) Field of Classification Search .................. 548/230; 549/417; 568/950
See application file for complete search history.

(56) References Cited

OTHER PUBLICATIONS

Dorwald F. A. Side Reactions in Organic Synthesis, 2005, Wiley: VCH, Weinheim p. IX of Preface p. 1-15.*
Marshall et al,(Journal of Organic Chemistry, 1998, 63, 7885-7892.*
Gunasekera, S.P., "Semisynthetic analogues of the microtubule-stabilizing agent discodermolide: preparation and biological activity," J. Nat. Prod., 2002, 65, 1830-1837.
Gunasekera, S.P., et al., "Discodermolide: A new bioactive polyhydroxylated lactone from the marine spong *Discodermia dissoluta*," J. Org. Chem., 1991, 56, 1346.
Hung, D.T., et al., "(+)-Discordermolide binds to microtubules in stoichiometric ratio to tubulin dimmers, blocks taxol binding and results in mitotic arrest," Chemi. & Biol., 1996, 3, 287-293.
Hung, D.T., et al., "Distinct binding and cellular properties of synthetic (+)- and (-) discodermolides," Chem. & Biol., 1994, 1, 67-71.

Longley, R.E., et al., "Discodermolide—a new, marine-derived immunosuppressive compound," Transplantation, 1991, 52, 650-656.
Longley, R.E., et al., "Discodermolide-a new, marine-derived immunosuppressive compound," Transplantation, 1991, 52, 656-661.
Longley, R.E., et al., "Immunosuppression by discodermolide," Ann. N.Y. Acad. Sci., 1993, 696, 94-107.
Nerenberg, J.B., et al., "Total synthesis of the immunosuppressive agent (-)-discodermolide," J. Am. Chem. Soc., 1993, 115, 12621-12622.
ter Haar, E., et al., "Discodermolide, a cytotoxic marine agent that stabilizes microtubules more potently than taxol," Biochemistry, 1996, 35, 243-250.
Welsenberg, R.C., "Microtubule formation in vitro in solutions containing low calcium concentrations," Science, 1972, 177, 1104-1105.

* cited by examiner

*Primary Examiner*—D. Margaret Seaman
*Assistant Examiner*—Nizal S Chandrakumar
(74) *Attorney, Agent, or Firm*—Woodcock Washburn, LLP

(57) ABSTRACT

Processes for synthesizing a compound of Formula (I) are provided by reacting a compound of Formula (i) with a compound of Formula (xx).

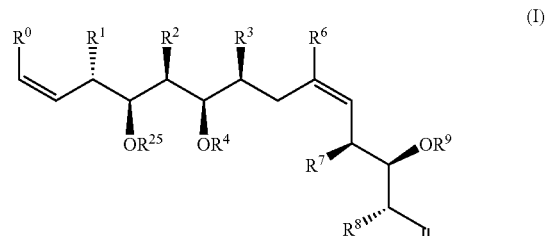

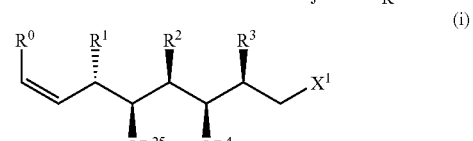

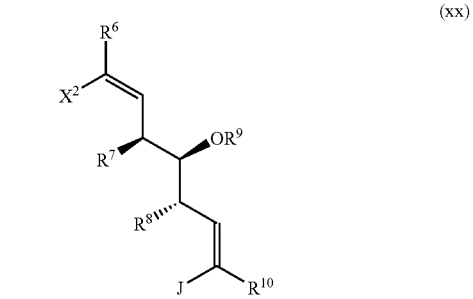

25 Claims, No Drawings

SYNTHESIS OF DISCODERMOLIDE AND VARIANTS THEREOF

RELATED APPLICATIONS DATA

This application is the National Stage of International Application No. PCT/US2004/033473, filed Oct. 12, 2004, which claims the benefit of U.S. Provisional Application No. 60/510,097, filed Oct. 9, 2003, the disclosure of which is incorporated herein by reference in it's entirety.

GOVERNMENT SUPPORT

Certain aspects of this invention may have been supported by Grant No. DADM 7-00-1-0404 awarded by the U.S. Army.

FIELD OF THE INVENTION

This invention relates to compounds which mimic the chemical and/or biological activity of discodermolide, and to methods and intermediates useful in their preparation.

BACKGROUND OF THE INVENTION

In 1990, Gunasekera and co-workers at the Harbor Branch Oceanographic Institute reported the isolation of (+)-discodermolide (1), an architecturally novel metabolite of the marine sponge *Discodermia dissolute* (0.002% w/w). (See, Gunasekera, et al., *J. Org. Chem.* 1990, 55, 4912. Correction: *J. Org. Chem.* 1991, 56, 1346).

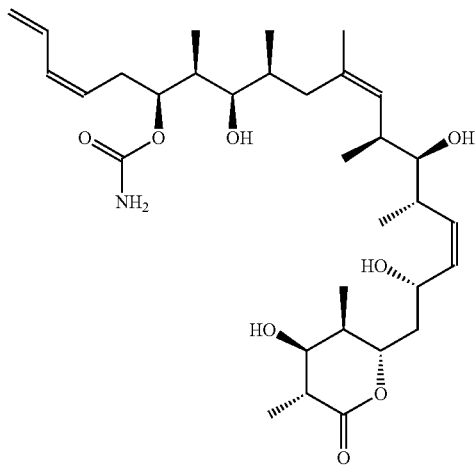

Initial studies revealed that (+)-discodermolide suppresses both the two-way mixed-lymphocyte reaction and the concanavalin A-induced mitogenesis of murine splenocytes in vitro with no associated cytotoxicity. Moreover, (+)-1 suppresses the in vivo graft-vs.-host splenomegaly response induced by injection of parental splenocytes into F1 recipient mice, with potency intermediate between those of cyclosporin A and FK506. (Longley, et al., *Transplantation* 1991, 52, 650; Longley, et al., *Transplantation* 1991, 52, 656; Longley, et al. *Ann. N.Y. Acad. Sci.* 1993, 696, 94). These findings stimulated the recent discovery that (+)-1 arrests cell development at the M phase by binding and stabilizing mitotic spindle microtubules; thus discodermolide resembles taxol in its mode of action, but the microtubule binding affinity of 1 is much higher. (ter Haar, et al., *Biochemistry* 1996, 35, 243; Hung, et al., *Chemi. & Biol.* 1996, 3, 287). These and other results suggest that (+)-discodermolide holds considerable promise as an anticancer agent. The scarcity of natural material however has precluded a complete evaluation of its biological profile.

The absolute configuration of discodermolide remained undefined until Schreiber et al. synthesized both antipodes of 1. (Nerenberg, et al. *J. Am. Chem. Soc.* 1993, 115, 12621; Hung, et al., *Chem. & Biol.* 1994, 1, 67). Interestingly, the unnatural (−) antipode also displays significant immunosuppressant activity.

There is, therefore, a need for improved synthetic methods for the preparation of discodermolide and compounds that mimic the chemical and/or biological activity of discodermolide.

SUMMARY OF THE INVENTION

The present invention includes processes for synthesizing compounds of formula I.

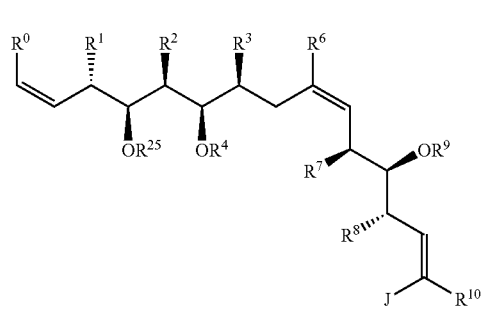

In an aspect of the present invention, the compounds of Formula I are formed by reacting a compound having formula i

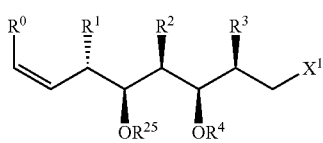

with a compound having formula xx

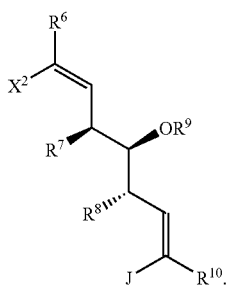

$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r(aryl)$ or $(CH_2)_r(heterocycle)$; wherein r is 0, 1, 2, 3, or 4. In some aspects of the present invention $R^0$ is $C_{1-6}$ alkyl or $C_{2-6}$ alkenyl. In certain aspects of the present invention, $R^0$ is preferably ethylenyl.

$R^1$, $R^2$, $R^3$, $R^6$, $R^7$, and $R^8$ are, independently, H or $C_1$-$C_{10}$ alkyl. In certain embodiments it is preferred that each one of $R^1$, $R^2$, $R^3$, $R^6$, $R^7$, and $R^8$ is, independently, H or $C_1$-$C_3$ alkyl, and more preferably $CH_3$.

The groups $R^4$ and $R^9$ are, independently, H or an acid labile hydroxyl protecting group. In embodiments where $R^4$ and $R^9$ is an acid labile protecting group, it is preferable that the acid labile hydroxyl protecting group is either tert-butyldimethylsilyl, triethylsilyl, methoxymethyl (MOM), methylthiomethyl, 2-methoxyethoxymethyl, acetyl, benzyloxymethyl, 2-(trimethylsilyl)ethoxymethyl or allyl. In some aspects of the present invention where $R^4$ is an acid labile hydroxyl protecting group, $R^4$ is preferably tert-butyl dimethylsilyl. In certain aspects of the present invention where $R^9$ is an acid labile hydroxyl protecting group, $R^9$ is preferably methoxymethyl.

$R^{10}$ is hydrogen or $C_1$-$C_6$ alkyl. In some aspects of the present invention, it is preferred that $R^{10}$ is $CH_3$.

$R^{25}$ is either hydrogen or an oxidation labile hydroxyl protecting group. For embodiments where $R^{25}$ is an oxidation labile hydroxyl protecting group, $R^{25}$ is preferably para-methoxybenzyl.

$X^1$ and $X^2$ are leaving groups and are, independently, either a halogen, triflate, tosylate, or mesylate. $X^1$ and $X^2$ are preferably iodine.

The group J is one of the following moieties:

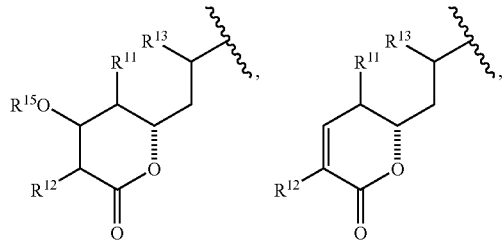

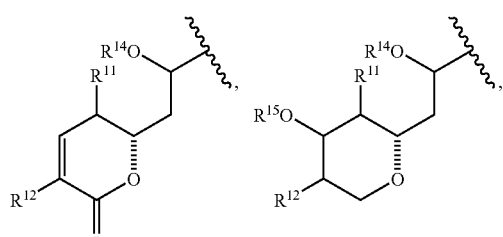

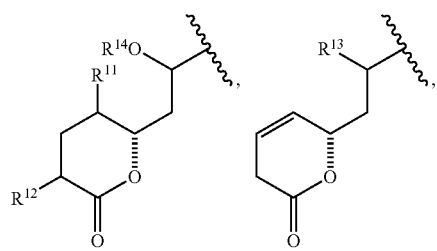

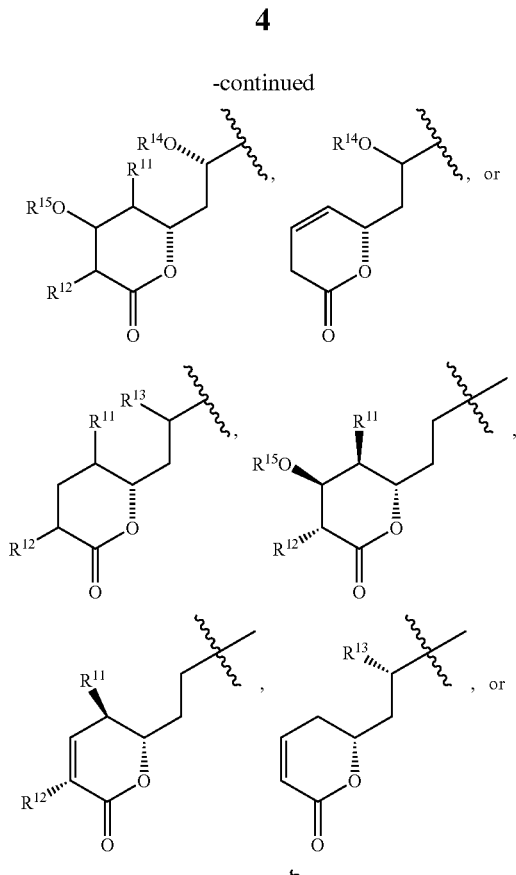

In one group of embodiments of the invention, it is preferable to select J from the following group:

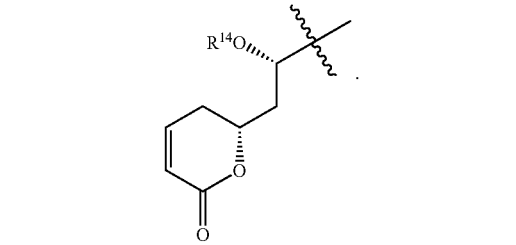

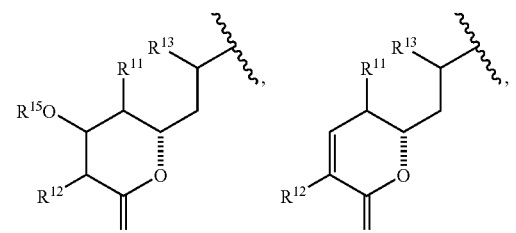

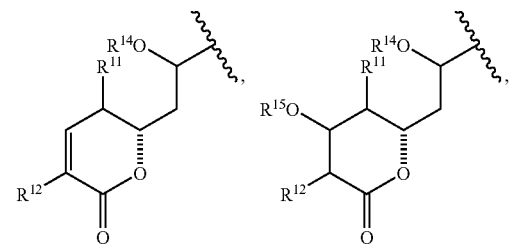

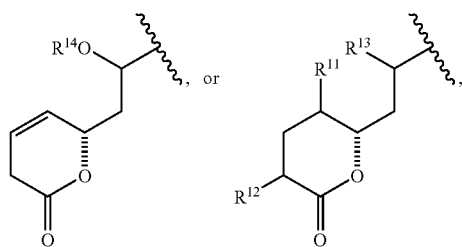

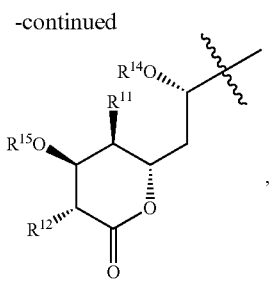

Preferably, J is

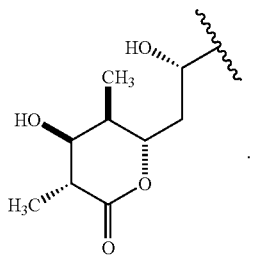

and more preferably

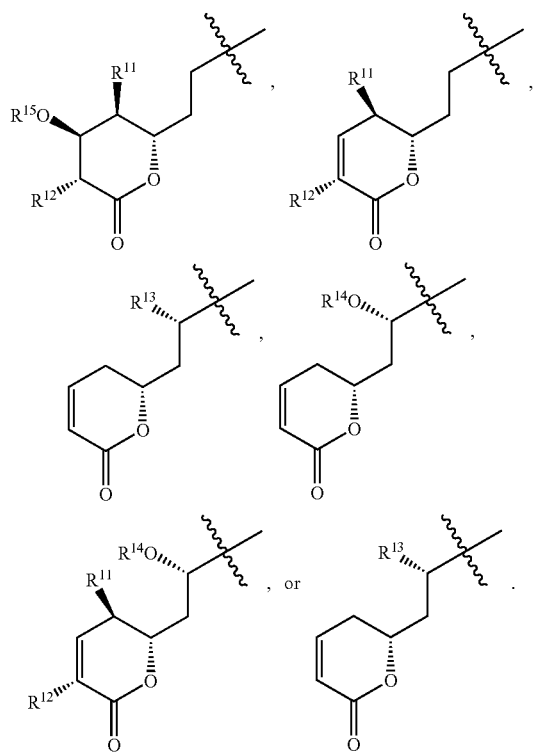

In some aspects of the present invention, it is preferable for J to be a moiety chosen from the following:

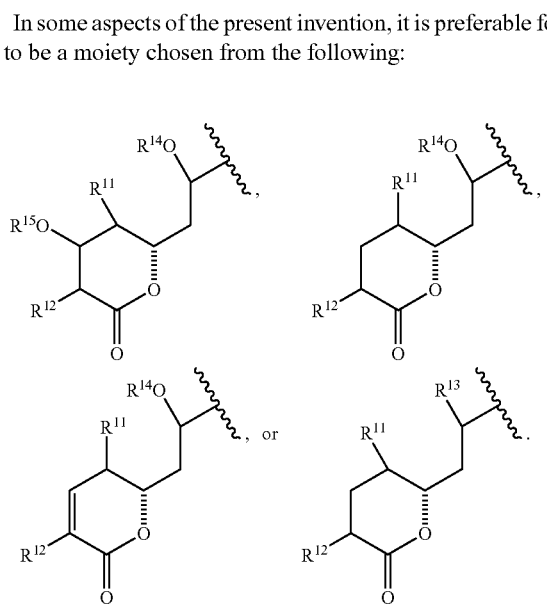

$R^{11}$, $R^{12}$ and $R^{13}$ are, independently, H or $C_1$-$C_{10}$ alkyl. In certain aspects of the present invention, preferably, $R^{11}$, $R^{12}$ and $R^{13}$ are, independently, H or $C_1$-$C_3$ alkyl, and even more preferably $CH_3$.

$R^{14}$ and $R^{15}$ are, independently, H or an acid labile hydroxyl protecting group. In certain aspects of the present invention, it is preferable that $R^{14}$ and $R^{15}$ are, independently, tert-butyldimethylsilyl or methoxymethyl.

The methods of the present invention also include contacting compounds of Formula i and Formula xx in the presence of a catalytically effective amount of a cross-coupling metal catalyst. The cross-coupling metal catalyst facilitates a carbon-carbon coupling of the two compounds under mild reaction conditions. The cross-coupling metal catalyst is nickel or palladium, or other metals known to have similar properties. Preferably, the cross-coupling metal catalyst is Pd(0).

In addition to the cross-coupling metal catalyst, the methods for synthesizing Formula I comprise contacting Formula i with a metallating agent. The metallating agent can be selected from a number of such agents useful for metal catalyzed cross-coupling, including boron, zinc, tin, lithium, or magnesium or aluminum, such as t-BuLi, Mg(0), Zn(0), MgBr2, SnBu3Cl, MeO-9-BBN or $ZnCl_2$. Preferably, the metallating agent is a compound containing boron or zinc. Even more preferably, the metallating agent is either MeO-9-BBN or $ZnCl_2$.

In another aspect of the present invention, provided are processes of synthesizing compounds of formula II

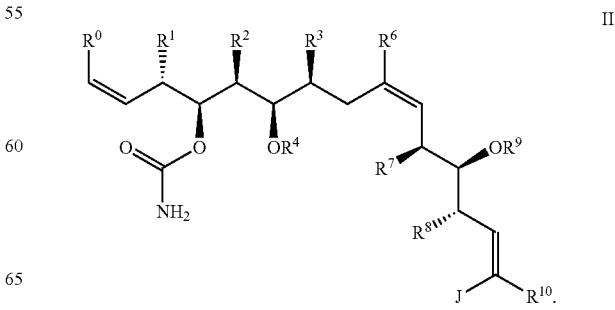

In certain aspects of the present invention, the compounds of Formula II are formed by deprotecting the compound of Formula I

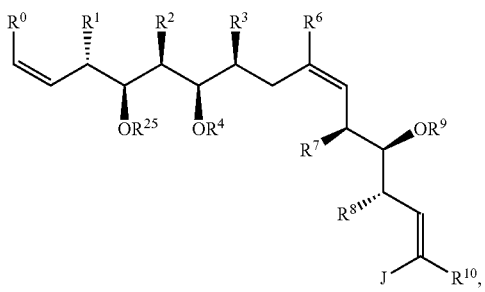

I which can be synthesized according to the methods of the present invention. The deprotecting step removes the $R^{25}$ group via oxidation, e.g., by adding 2,3-dichloro-5,6-dicyano-1,4-benzoquinone (DDQ). The deprotected compound of Formula I is contacted with $Cl_3CCONCO$. This step is commonly performed in the presence of a hydrolyzing agent, preferably $Al_2O_3$.

In another aspect of the present invention, there are processes for synthesizing compounds of Formula III

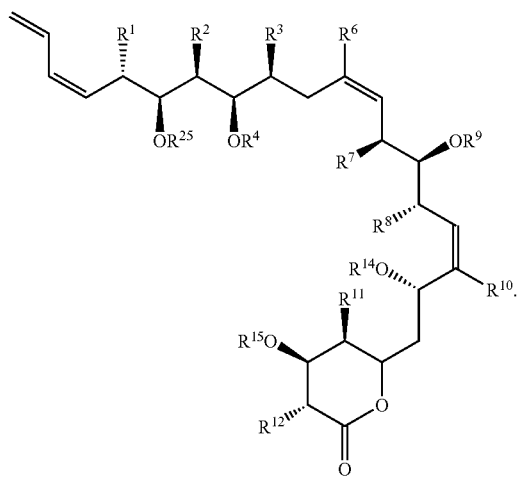

III

Such compounds may be formed by contacting dienes of Formula xi

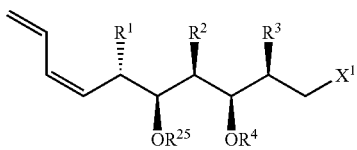

xi with lactones of formula xxi

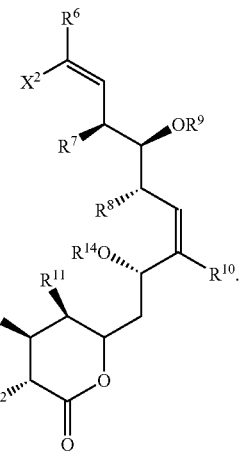

xxi

This process may be catalyzed by adding a metal cross-coupling catalyst in amounts effective to catalyze the reaction to substantial completion.

A further aspect of the present invention involves processes of synthesizing compounds of Formula IV

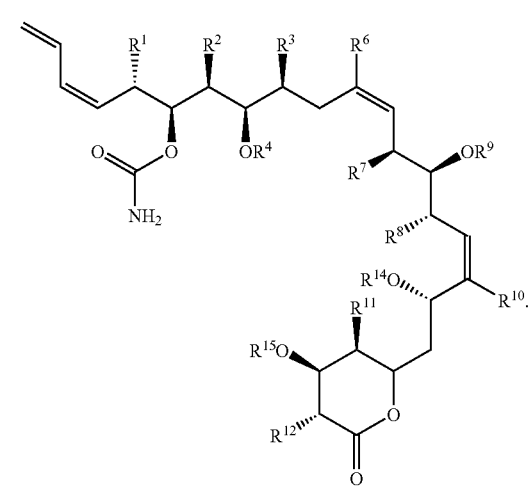

IV

Such compounds may be formed by deprotecting compounds of Formula III

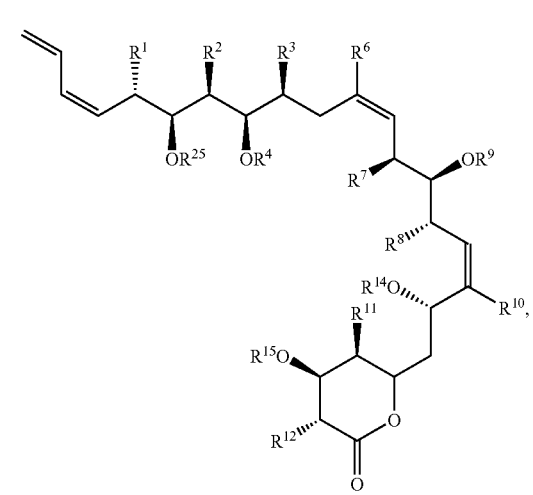

III which may be synthesized according to the methods of the present invention.

The deprotecting step removes the $R^{25}$ group via oxidation, e.g., by adding 2,3-dichloro-5,6-dicyano-1,4-benzoquinone (DDQ). The deprotected compound of Formula III may then be contacted with $Cl_3CCONCO$. This step is commonly performed in the presence of a hydrolyzing agent, preferably $Al_2O_3$.

In another aspect of the present invention, there are processes for synthesizing halogenated alkenyls of Formula i:

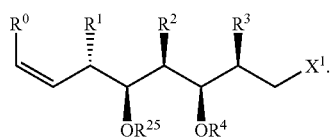

i $R^0$ may be bound to the carbon of the C=C in either cis or trans conformation. Such compounds can be formed by contacting alcohols of Formula iia

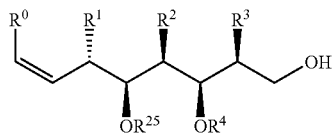

iia with $(X^1)_2$ in the presence of $P(R^{18})_3$. The group $R^{18}$ is $C_6$-$C_{14}$ aryl, and preferably, phenyl.

Alcohols of Formula iia can be synthesized by contacting an alkenyl of formula ii

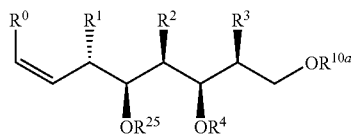

ii with a mild acid, e.g., a formic acid/ether solution. $R^{10a}$ is a hydroxyl protecting group, and preferably trityl.

The alkenyls of Formula ii may be synthesized by reacting an aldehyde of Formula iii:

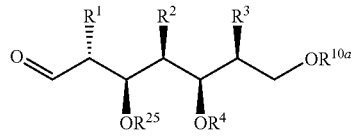

iii with $R^0CH_2$—$P(R^{18})_3X^1$, preferably in the presence of a base. In one particular set of embodiments, the alkenyl of formula ii has an $R^0$ that is $CH_3$=CH— and is synthesized by contacting a compound of formula iii with allyldiphenylphosphine. Preferably, this synthesis occurs in the presence of a strong base, e.g., t-BuLi, which can include the presence of $Ti(O_iPr)_4$, and is followed by the addition of an alkylhalide, preferably MeI.

The aldehydes of Formula iii may be synthesized by subjecting a compound of formula iv

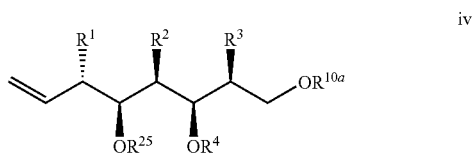

iv to ozonolysis. Preferably, ozonolysis is accomplished by adding $O_3$, sometimes in the presence of $PPh_3$.

The compounds of formula iv may be synthesized by a process comprising contacting a compound of formula v

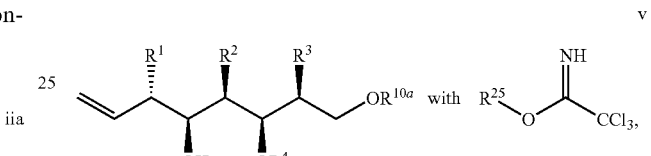

v preferably in the presence of a base. An example of such a base can be TfOH.

The compounds of formula v can be synthesized by a process comprising contacting a compound of formula vi

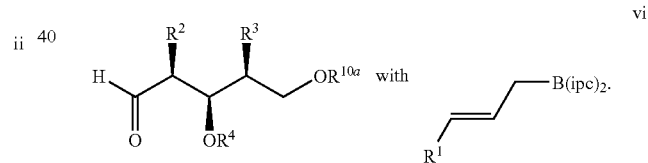

vi

This reaction is preferably performed in the presence of $BF_3$—$OEt_2$. Additionally,

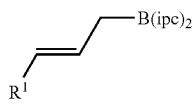

may be formed by reacting

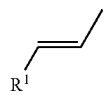

with tBuOK and nBuLi, followed by (−)-(ipc)$_2$B—OMe.

The compounds of formula vi may be synthesized by a process comprising contacting a compound of formula vii

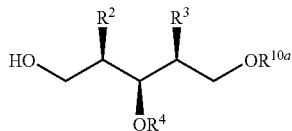

vii with an oxidizing agent. In one embodiment, the oxidizing agent is SO$_3$-pyr. The reaction may take place in the solvent DMSO.

The compounds of formula vii can be synthesized by a process comprising contacting compounds of formula viii

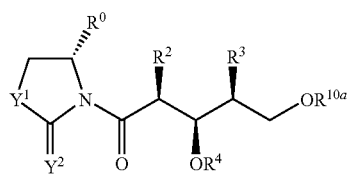

viii with a reducing agent, e.g., LiBH$_4$; wherein Y$^1$ and Y$^2$ are, independently, O or S.

The compounds of formulas viii and viii' may be synthesized by a process comprising protecting a hydroxyl moiety of compounds of formulas ix

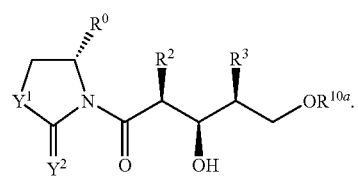

ix

This protecting step comprises replacing a hydrogen atom of a hydroxyl moiety with tert-butyldimethylsilyl, triethylsilyl, methoxymethyl, methylthiomethyl, 2-methoxyethoxymethyl, acetyl, benzyloxymethyl 2-(trimethylsilyl)ethoxymethyl or an allyl moiety.

The compounds of formulas ix and ix' can be synthesized by a process comprising contacting a compound of formula x

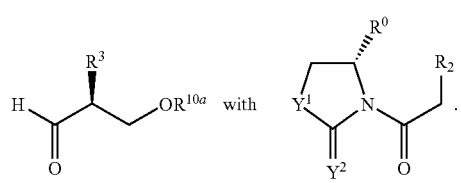

x

Such reactions are preferably performed in the presence of a base, such as Hunigs base, and can also include n-Bu$_2$B—OTf.

DEFINITIONS

As used herein, the following terms and expressions have the indicated meanings. It will be appreciated that the compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

"Stable compound" and "stable structure" are meant to indicate a compound that is sufficiently robust to survive isolation to a useful degree of purity from a reaction mixture, and formulation into an efficacious therapeutic agent. Stable compounds are preferred in accordance with the present invention.

The compounds disclosed herein may be substituted or unsubstituted. "Substituted" is intended to indicate that one or more hydrogens of the identified moiety are replaced with a selection from the indicated group(s), provided that the normal valency in the identified moiety is not exceeded, and that the substitution results in a stable compound. When a substituent is =O (a keto group), then two hydrogens on the implicated carbon atom are replaced. By way of illustration, when a carbon ring containing one oxygen is substituted on the carbon adjacent to the oxygen =O, a lactone is formed.

"Alkyl" refers to an optionally substituted, saturated straight, or branched, hydrocarbon radical having from about 1 to about 20 carbon atoms (and all combinations and subcombinations of ranges and specific numbers of carbon atoms therein). Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl. The terms such as "C$_{1-6}$ alkyl" is used herein to mean alkyl chains containing a certain range of carbon atoms, in this case 1 to 6 carbon atoms.

"Alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined. The terms such as "C$_{2-6}$ alkenyl" is used herein to mean alkenyl chains containing a certain range of carbon atoms, in this case 2 to 6 carbon atoms. A "diene" refers to a straight or branched carbon chain comprising at least two double bonds, but preferably two double bonds only.

"Alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined. The terms such as "C$_{2-6}$ alkynyl" is used herein to mean alkynyl chains containing a certain range of carbon atoms, in this case 2 to 6 carbon atoms.

The term "cycloalkyl," or "carbocyclic ring," refers to an optionally substituted, mono-, di-, tri-, or other multicyclic alicyclic ring system having from about 3 to about 20 carbon atoms (and all combinations and subcombinations of ranges and specific numbers of carbon atoms therein). In some preferred embodiments, the cycloalkyl groups have from about 3 to about 8 carbon atoms. Multi-ring structures may be bridged or fused ring structures, wherein the additional groups fused or bridged to the cycloalkyl ring may include optionally substituted cycloalkyl, aryl, heterocycloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

An "aryl" or "aromatic" moiety refer to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

The term "heterocycle," or alternatively, a "heterocycloalkyl," is used herein to refer to a 3 to 20 membered, and more preferably 5 to 8 membered cycloalkyl group in which one to three carbon atoms of the cycloalkyl group are replaced with a heteroatom. A "heteroatom" is a non-carbon atom including oxygen, nitrogen, or sulfur that can replace a carbon atom of a cycloalkyl group. The heterocycloalkyl group may be saturated or partially saturated, and may be monocyclic or bicyclic (such as bridged). Preferably, the heterocycloalkyl is monocyclic. The heterocycloalkyl group may optionally be substituted.

"Halo" and "halogen" each refers to a fluoro, chloro, bromo, or iodo moiety, with iodo being preferred.

"Haloalkyl" is intended to include both branched and straight-chain saturated aliphatic hydrocarbon groups having the specified number of carbon atoms, substituted with 1 or more halogen. Examples of haloalkyl groups include, but are not limited to, trifluoromethyl, trichloromethyl, pentafluoroethyl, and pentachloroethyl groups.

The term "cross-coupling metal catalyst" refers to a metal that catalyzes carbon-carbon coupling of the respective carbon atoms of two compounds. Typically, the reaction allows for mild reaction conditions. The cross-coupling metal catalyst is nickel or palladium, or other metals known to have similar properties. Preferably, the cross-coupling metal catalyst is Pd(0).

A "metallating agent" is used herein to mean a compound containing a metal that may complex with a hydrocarbon molecule and assist in the metal catalyzed cross-coupling reaction. The metallating agent can be selected from a number of such agents useful for metal catalyzed cross-coupling, including boron, zinc, tin, lithium, or magnesium or aluminum, such as t-BuLi, Mg(0), Zn(0), MgBr2, SnBu3Cl, MeO-9-BBN or $ZnCl_2$. Preferably, the metallating agent is a compound containing boron or zinc. Even more preferably, the metallating agent is either MeO-9-BBN or $ZnCl_2$.

A "catalytically effective amount" refers to a minimum amount of catalyst required to result in the cross-coupling of two compounds, as described herein.

The target compounds and intermediates of the present invention may contain protecting groups. Protecting groups are known per se as chemical functional groups that can be selectively appended to and removed from functionality, such as hydroxyl and amine groups, present in a chemical compound to render such functionality inert to certain chemical reaction conditions to which the compound is exposed. See, e.g., Greene and Wuts, Protective Groups in Organic Synthesis, 2d edition, John Wiley & Sons, New York, 1991.

A "hydroxyl protecting group" refers to a class of groups that may be used to replace a hydrogen atom of a hydroxyl group to protect the hydroxyl group from unwanted chemical modifications due to a variety of reaction conditions, such as alkyl, cycloalkyl and aryl groups, which replace the hydroxyl group with an ether group, e.g., trityl. One sub-class of hydroxyl protecting group is an "acid labile hydroxyl protecting group," which refers to hydroxyl protecting groups that may be removed, or deprotected, in the presence of an acid, such as formic acid. An acid labile hydroxyl protecting group may be selected from the following: tert-butyldimethylsilyl, triethylsilyl, methoxymethyl (MOM), methylthiomethyl, 2-methoxyethoxymethyl, acetyl, benzyloxymethyl, 2-(trimethylsilyl)ethoxymethyl or allyl. Another sub-class of hydroxyl protecting group is an "oxidation labile hydroxyl protecting group," or an "oxidatively labile group," which refers to hydroxyl protecting groups that may be removed, or deprotected, in the presence of an oxidizing agent, such as 2,3-dichloro-5,6-dicyano-1,4-benzoquinone (DDQ). Preferably, the oxidation labile hydroxyl protecting group is para-methoxybenzyl.

Within the parameters of the present invention, it is understood that one sub-class of hydroxyl protecting group is not mutually exclusive of the other. In particular, a particular hydroxyl protecting group that is classified under one sub-class does not necessarily exclude that protecting group from another subclass. For example, trityl is referred to as a hydroxyl protecting group, but trityl may also be used as an acid labile hydroxyl protecting group.

The present invention contemplates the compounds disclosed herein to be used as prodrugs. The term "prodrug" is intended to include any molecule that is transformed into a compound according to any compound of the present invention in vivo following administration to a mammal. A prodrug form of a compound of the present invention can be prepared, for example, by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammal subject, cleaves to form a free hydroxyl or free amino, respectively. Examples of prodrugs include, but are not limited to, acetate, formate and benzoate derivatives of alcohol and amine functional groups in the compounds of the present invention, and the like.

"Therapeutically effective amount" is intended to include an amount of a compound of the present invention or an amount of the combination of compounds claimed effective produce the desired effect. Such effects include, for example, the stablization of microtubules or any other beneficial or therapeutic effect.

The compounds of the subject invention have utility for the treatment of cancer, and as tubulin polymerizers and as microtubule stabilization agents. In particular examples of uses of the compounds of the present invention are methods of treating animals hosting cancer cells including, for example, inhibiting the growth of tumor cells in a mammalian host. More particularly, the compounds of the present invention can be used for inhibiting in a human the growth of tumor cells, including cells of breast, colon, CNS, ovarian, renal, prostate, liver, pancreatic, uterine, or lung tumors, as well as human leukemia or melanoma cells. These specific diseases are described for exemplary purposes only and the scope of the present invention is not limited thereby.

The compounds of the present invention may also be useful for inhibiting the growth of multidrug resistant cells, particularly cells resistant to taxanes, for example paclitaxel. Also, the compounds may be useful for inhibiting the growth of a cancer cell, such as a leukemia cell, a lymphoma cell and a solid tumor cell. The compounds of the present invention also may be useful for promoting apoptosis in a multidrug resistant cells. The cancer cells can be a cell derived from a tumor that is selected from the group of tumors consisting of lung, prostate, colon, breast, ovarian, kidney, brain, pancreatic esophageal, head and neck, gastric, and liver tumors.

The compounds of the subject invention may be utilized in connection with pharmaceutically acceptable carriers or diluents. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The compounds of the present invention can be admixed with carriers, excipients, and/or diluents to form novel compositions. Such compositions can be used in prophylactic, diagnostic, and/or therapeutic techniques. By administering an effective amount of such a composition, prophylactic or therapeutic responses can be produced in a human or some other type mammal. It will be appreciated that the production of prophylactic or therapeutic responses includes the initiation or enhancement of desirable responses, as well as the mitigation, cessation, or suppression of undesirable responses. The compositions of the invention are expected to find use, for example, in the inhibition of undesired cell proliferation (e.g., cancer) and in the inhibition of rejection in organ transplantation procedures. (See, e.g., Longley, et al., *Transplantation* 1991, 52, 650 and 656).

Compositions of the invention can be prepared by any of the methods well known in the pharmaceutical art, for example, as described in *Remington's Pharmaceutical Sciences* (Mack Pub. Co., Easton, Pa., 1980). The compositions can include a compound of the invention as an active ingredient in admixture with an organic or inorganic carrier or excipient suitable, for example, for oral administration. Other suitable modes of administration will be apparent to those skilled in the art. The compound of the invention can be compounded, for example, with the usual non-toxic, pharmaceutically acceptable carriers for tablets, pellets, capsules, solutions, suppositories, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The compound of the invention is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in appropriately soluble (e.g., gelatin) capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, glycerin and various like combinations thereof.

For parenteral administration, suspensions containing a compound of the invention in, for example, aqueous propylene glycol can be employed. The suspensions should be suitably buffered (preferably pH>8) if necessary and the liquid diluent first rendered isotonic. The aqueous suspensions are suitable for intravenous injection purposes. The preparation of such suspensions under sterile conditions is readily accomplished by standard pharmaceutical techniques well-known to those skilled in the art. Additionally, it is possible to administer the compounds of the invention topically and this may preferably be done by way of creams, jellies, gels, pastes, ointments and the like, in accordance with standard pharmaceutical practice.

The compounds of the invention can be employed as the sole active agent in a pharmaceutical composition or can be used in combination with other active ingredients, e.g., other agents useful in diseases or disorders.

The amount of active ingredient that is to be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day.

The concentrations of the active ingredient in therapeutic compositions will vary depending upon a number of factors, including the dosage of the drug to be administered, the chemical characteristics (e.g., hydrophobicity) of the active ingredient, and the route of administration. Typical dose ranges are from about 285 μg/kg of body weight per day in three divided doses; a preferred dose range is from about 42 μg/kg to about 171 μg/kg of body weight per day. The preferred dosage to be administered is likely to depend on such variables as the type and extent of progression of the disease or disorder, the overall health status of the particular patient, the relative biological efficacy of the compound selected, and formulation of the compound excipient, and its route of administration, as well as other factors, including bioavailability, which is in turn influenced by several factors well known to those skilled in the art.

The present invention includes the use of a discodermolide or a mimic thereof, such as compounds of Formula IV, in combination therapy with another agent, especially an anticancer therapeutic, including, but not limited to, Taxol®. Thus, component (a) discodermolide or a mimic thereof and component (b) Taxol may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more than one agent, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70-80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

All reactions were carried out in oven-dried or flame-dried glassware under an argon atmosphere, unless otherwise noted. All solvents were reagent grade. Diethyl ether and tetrahydrofuran (THF) were freshly distilled from sodium/benzophenone under argon before use. Dichloromethane, benzene and diisopropyl amine were freshly distilled from calcium hydride before use. Triethylamine and diisopropylethylamine were distilled from calcium hydride and stored over potassium hydroxide. Hexamethylphosphoramide was freshly distilled from calcium hydride. Anhydrous pyridine, dimethylformamide and dimethyl sulfoxide were purchased from Aldrich and used without purification. n-Butyllithium and t-butyllithium were purchased from Aldrich and standardized by titration with diphenylacetic acid.

Unless stated otherwise all reactions were magnetically stirred and monitored by thin layer chromatography using 0.25 mm E. Merck pre-coated silica gel plates. Flash column chromatography was performed with the indicated solvents using silica gel-60 (particle size 0.040-0.062 mm) supplied by E. Merck. Yields refer to chromatographically and spectroscopically pure compounds, unless otherwise stated.

All melting points were determined on a Bristoline heated-stage microscope or a Thomas-Hoover apparatus and are corrected. The IR and NMR were obtained for $CHCl_3$ and $CDCl_3$ solutions respectively unless otherwise noted. Infrared spectra were recorded with a Perkin-Elmer Model 283B spectrometer using polystyrene as an external standard. Proton NMR spectra were recorded on a Bruker AM-500 spectrometer. Carbon-13 NMR spectra were recorded on a Bruker AM-500 or AM-250 spectrometer. Chemical shifts are reported relative to internal tetramethylsilane (d 0.00) for proton and chloroform δ 77.0) or benzene (δ 128.0) for carbon-13.

Optical rotations were obtained with a Perkin-Elmer model 241 polarimeter in the solvent indicated. High-resolution mass spectra were obtained at the University of Pennsylvania Mass Spectrometry Service Center on either a VG micromass 70/70H high resolution double-focusing electron impact/chemical ionization spectrometer or a VG ZAB-E spectrometer. Microanalyses were performed by Robertson Laboratories, Madison, N.J. Single-crystal X-ray diffraction structure determination were performed at the University of Pennsylvania using an Enraf Nonius CAD-4 automated diffractometer. High performance liquid chromatography (HPLC) was performed using a Ranin component analytical/semi-prep system.

All drugs were dissolved in sterile DMSO and stored at −20° C. Microtubule protein (MTP) was purified by 2 cycles of temperature-dependent assembly-disassembly from calf brain and stored in liquid nitrogen. See, for example, Welsenberg, R. C., "Microtubule formation in vitro in solutions containing low calcium concentrations", *Science*, 1972, 177, 1104-1105. The concentration of tubulin in the microtubule protein preparation was approximately 85%.

Synthesis

The methods of the present invention are generally directed to the synthesis of compounds of Formula I, represented by Scheme I.

Scheme I
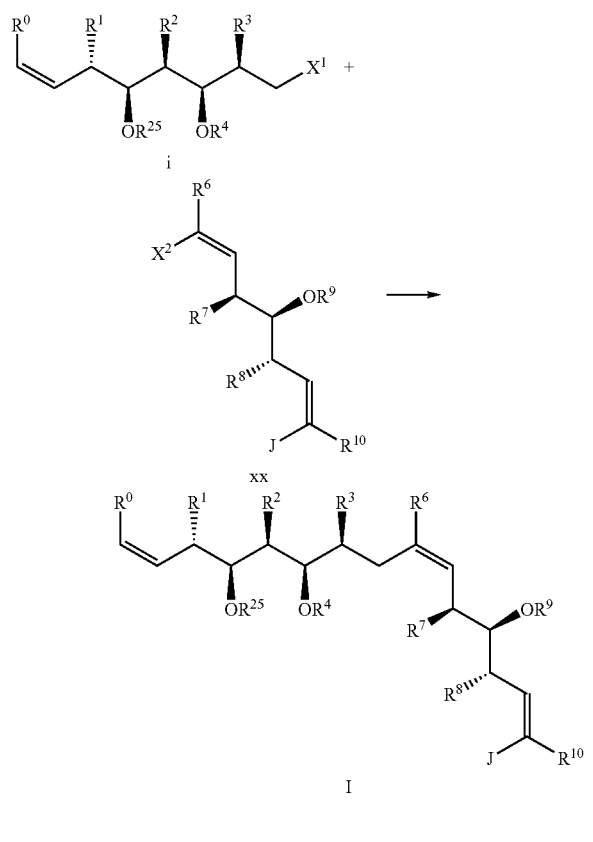
Preferably, the methods are directed to the synthesis of compounds of Formula III, which are represented by Scheme II.
Scheme II
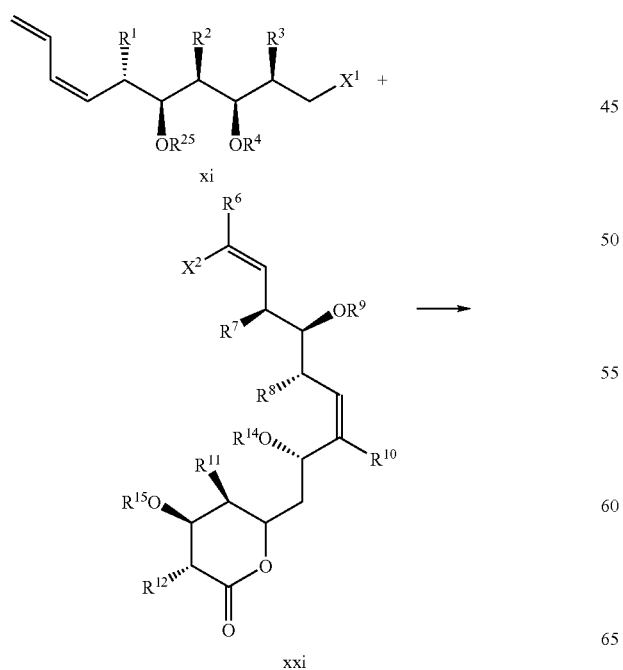
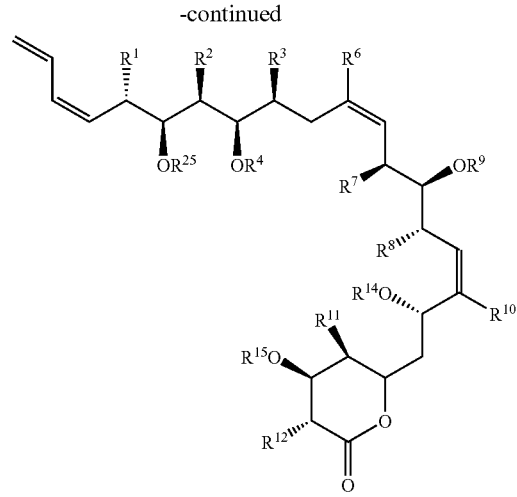
In particular embodiments, the present invention provides methods of synthesis of compounds of Formula (+)-ABC
(+)-ABC
represented by scheme III.
Scheme III
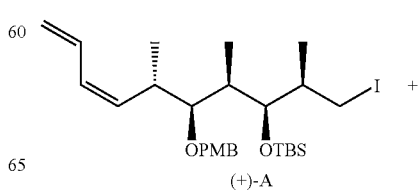
(+)-A -continued
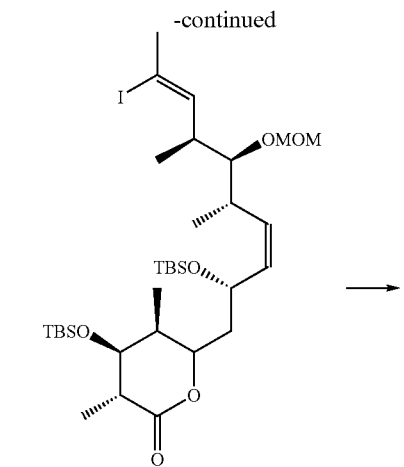
(+)-BC
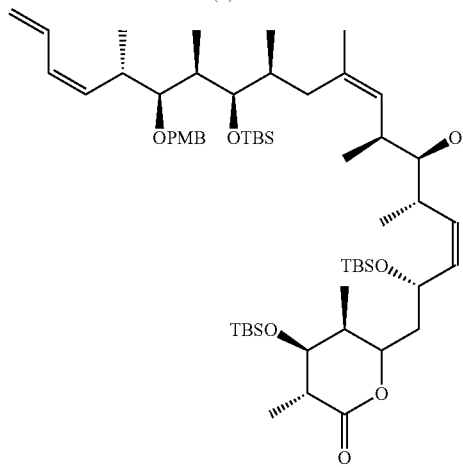
(+)-ABC
Some aspects of the present invention are directed to methods of synthesis of compounds of Formula i, which are reactants for the synthesis of compounds of Formula I. These methods represented by Scheme 1a.
Scheme 1a
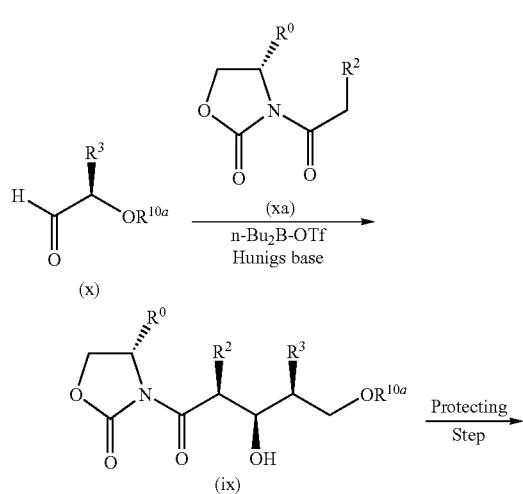
-continued
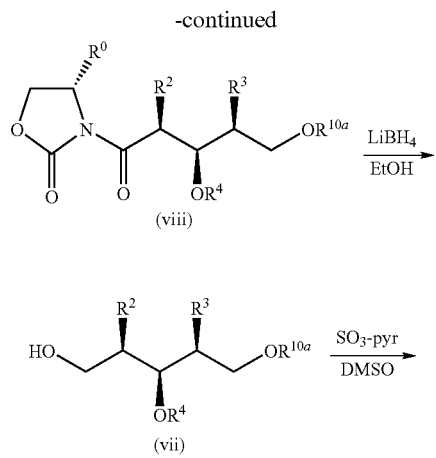
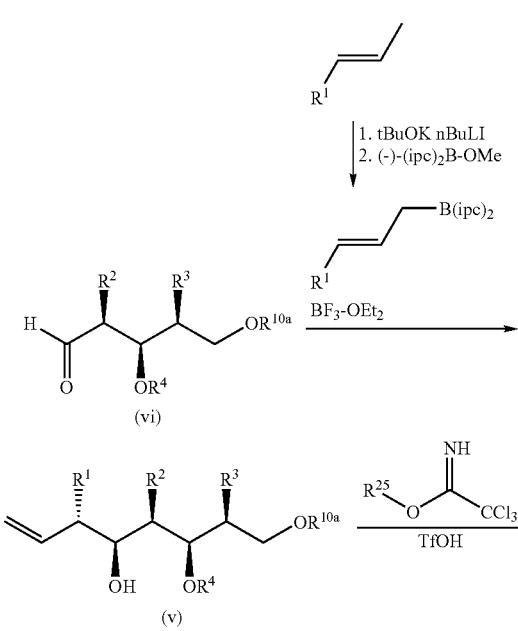
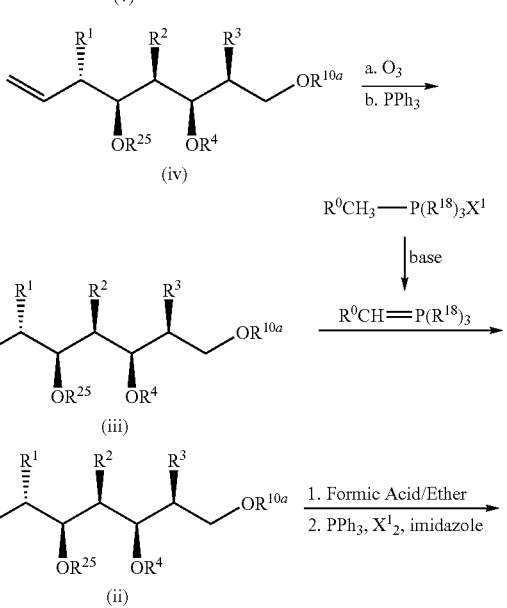

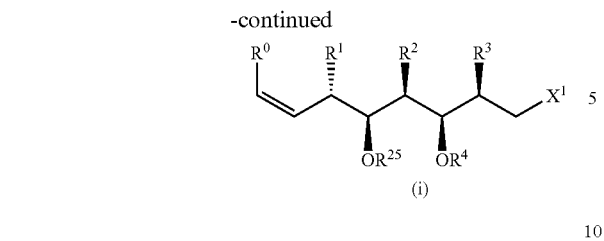

(i)

In other aspects of the present invention, methods are provided for the synthesis of compounds of Formula xi, which are reactants for the synthesis of compounds of Formula III. These methods are represented by Scheme 1b.

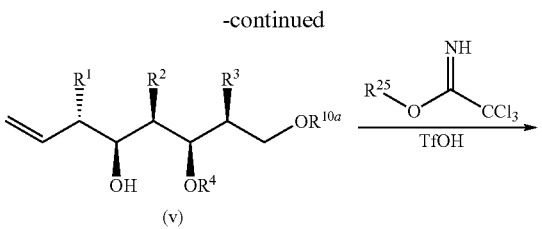

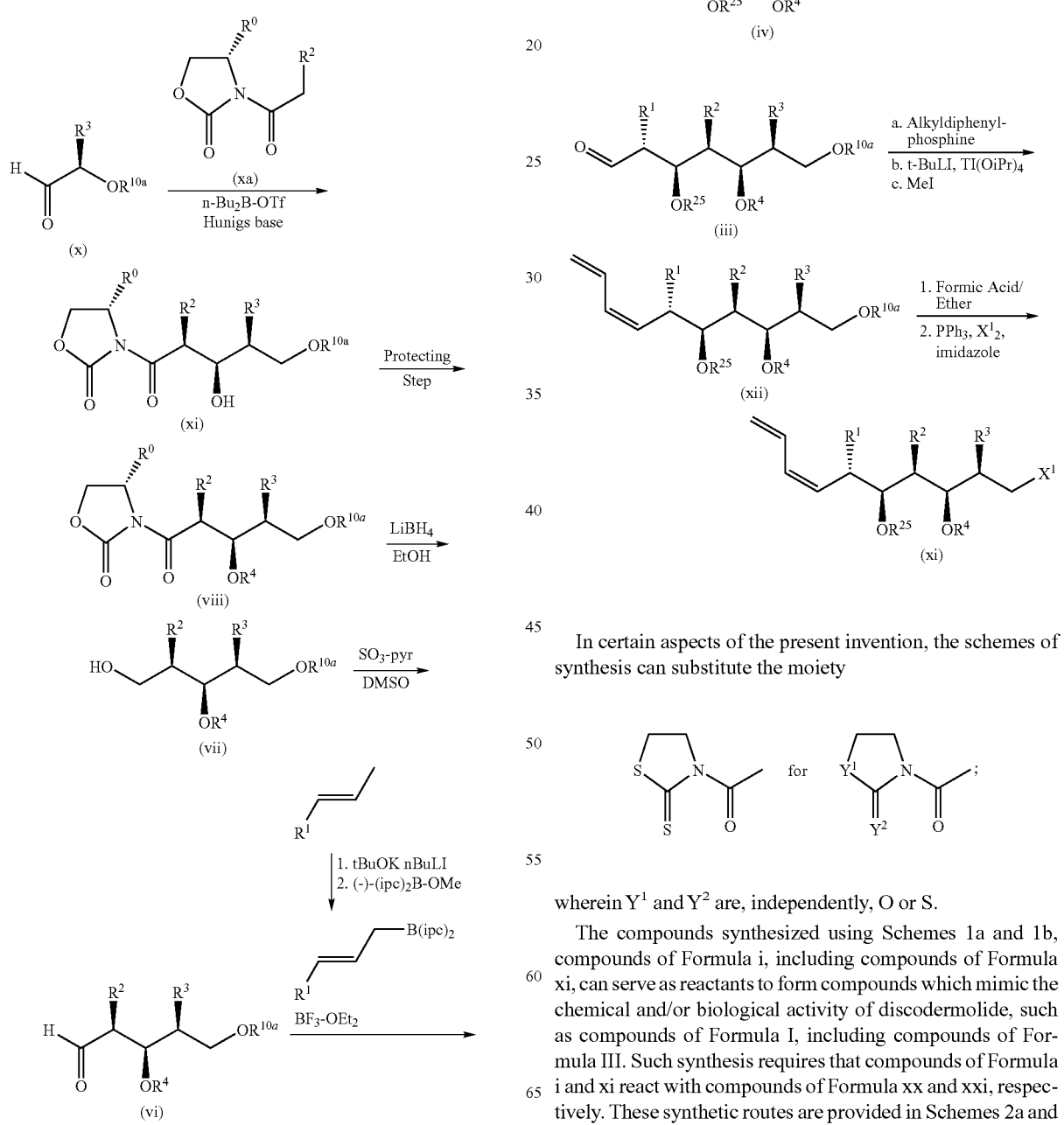

In certain aspects of the present invention, the schemes of synthesis can substitute the moiety wherein $Y^1$ and $Y^2$ are, independently, O or S.

The compounds synthesized using Schemes 1a and 1b, compounds of Formula i, including compounds of Formula xi, can serve as reactants to form compounds which mimic the chemical and/or biological activity of discodermolide, such as compounds of Formula I, including compounds of Formula III. Such synthesis requires that compounds of Formula i and xi react with compounds of Formula xx and xxi, respectively. These synthetic routes are provided in Schemes 2a and 2b and Schemes 3a and 3b, respectively.

Scheme 2a
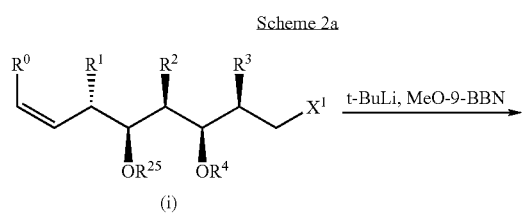
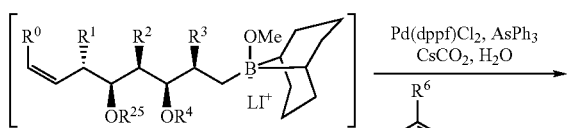
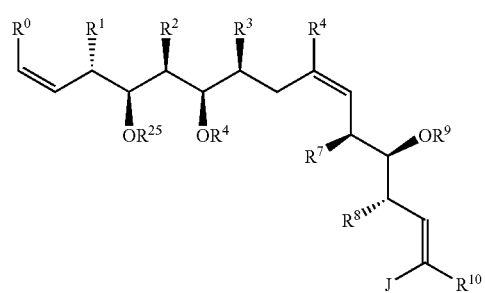
Scheme 2b
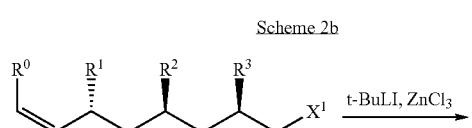
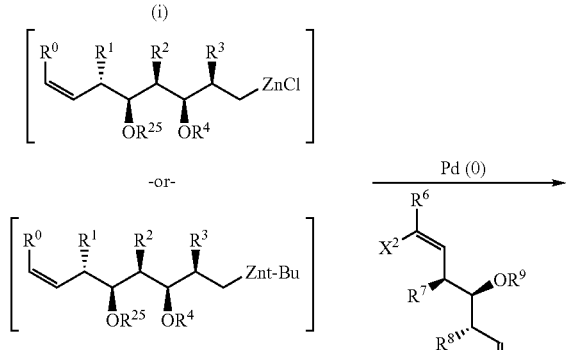
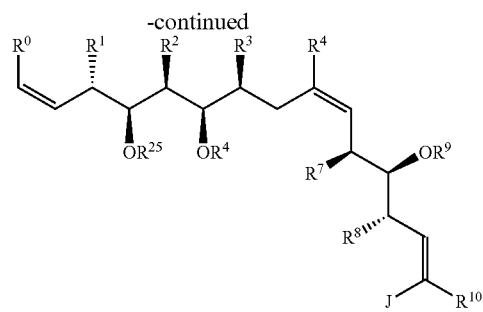
Scheme 3a
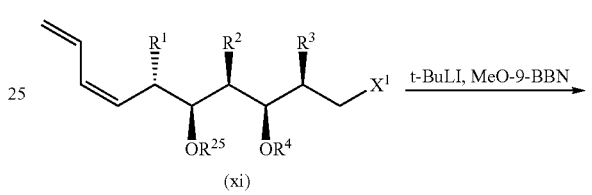
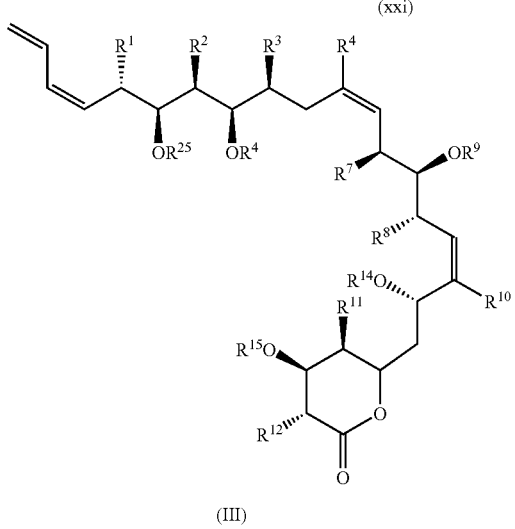

Scheme 3b
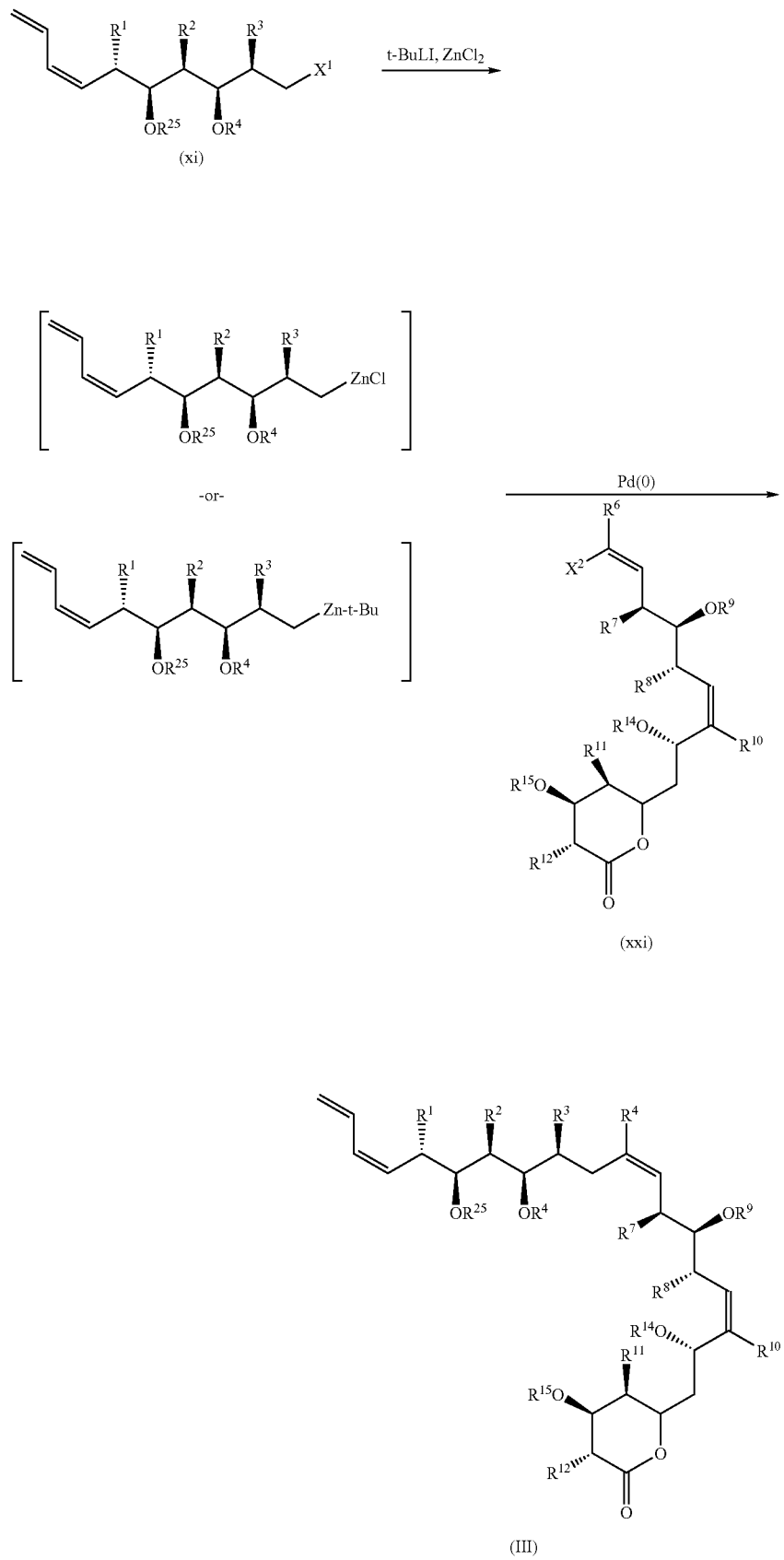

In one preferred embodiment, the methods of the present invention are directed to the synthesis of (+)-ABC, and the synthesis of one of the reactants for such synthesis, Compound A. The method for the synthesis of (+)-ABC and A can be found in Schemes 4a and 4b, respectively.
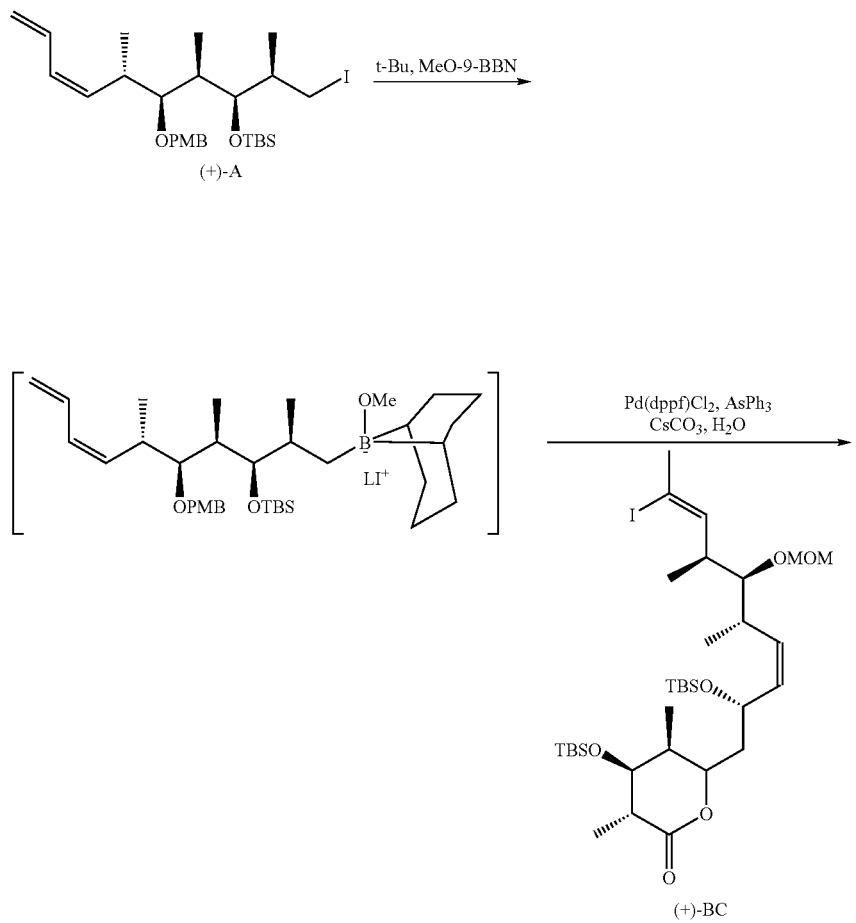
Scheme 4a
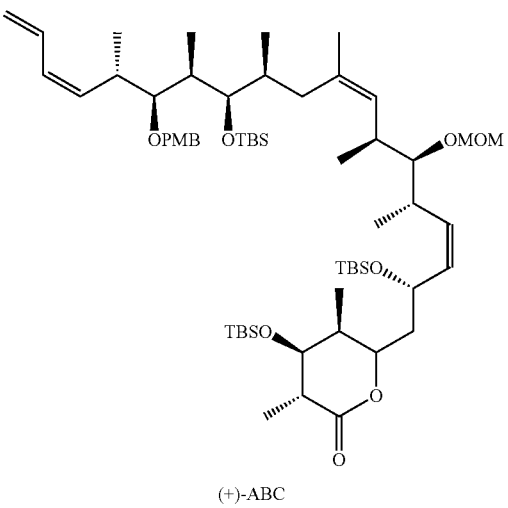

Scheme 4b

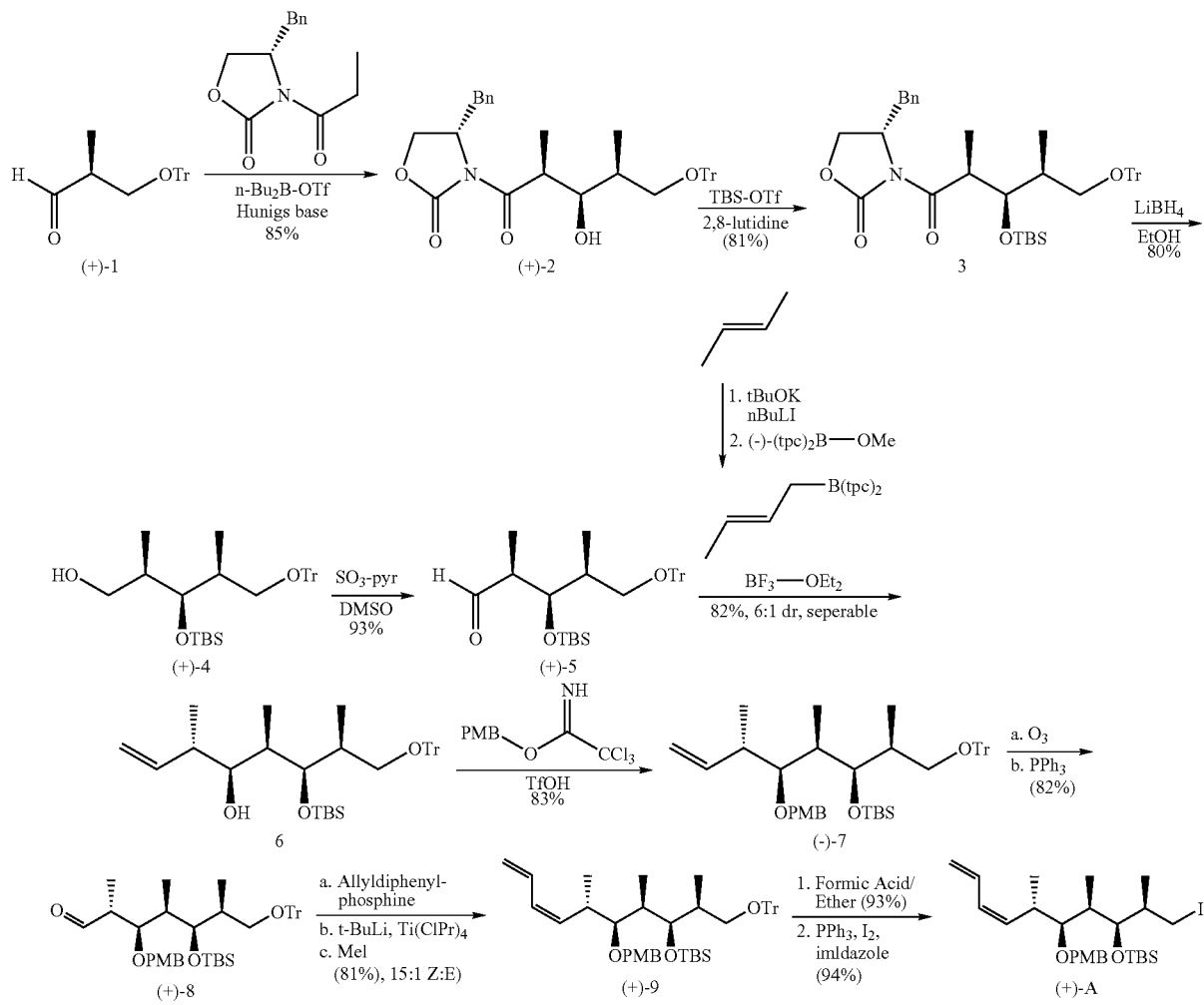

In certain other embodiments of the present invention, there are provided the following schemes for the synthesis of (+)-discodermolide. Also, there are provided schemes for the synthesis of the Fragments that are reactants for the syntheses for the formation of discodermolide.

Fourth-Generation Synthesis of (+)-Discodermolido
(Streamlined Fragment A, New Fragment B)

Common Precursor

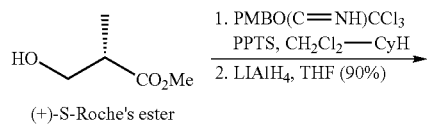

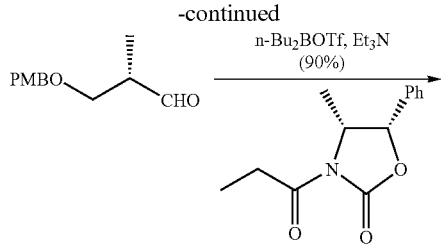

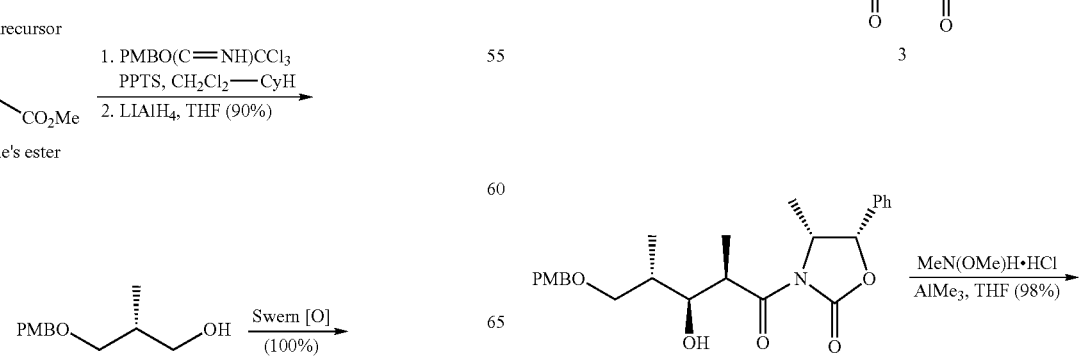

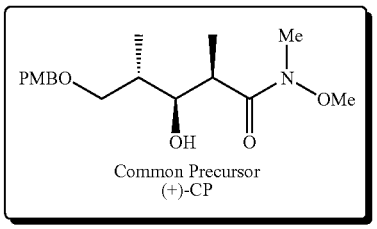

Total Steps: 5
Overall Yield: 72%

Common Precursor
(+)-CP

Bifunctional Fragment B Synthesis

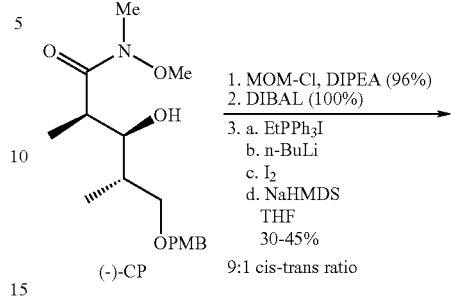

1. MOM-Cl, DIPEA (96%)
2. DIBAL (100%)
3. a. EtPPh₃I
    b. n-BuLi
    c. I₂
    d. NaHMDS
       THF
       30-45%
9:1 cis-trans ratio (+)-A synthesis

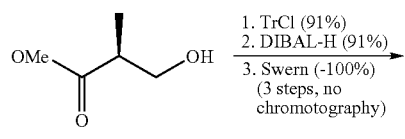

1. TrCl (91%)
2. DIBAL-H (91%)
3. Swern (~100%)
(3 steps, no chromotography)

(+)-S-Roche's Ester

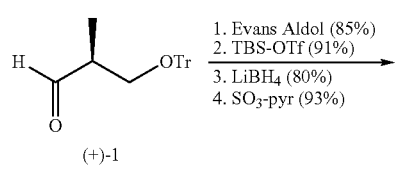

1. Evans Aldol (85%)
2. TBS-OTf (91%)
3. LiBH₄ (80%)
4. SO₃-pyr (93%)

(+)-1

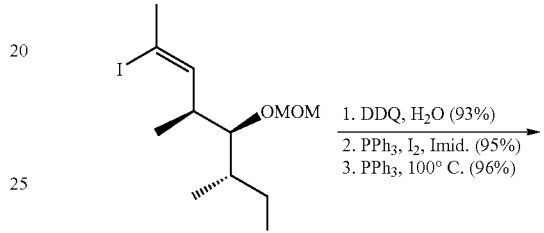

1. DDQ, H₂O (93%)
2. PPh₃, I₂, Imid. (95%)
3. PPh₃, 100° C. (96%)

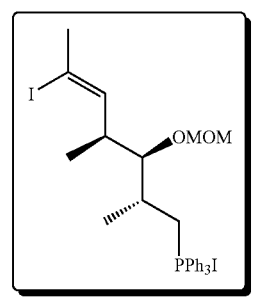

Total Steps (from Roches Ester): 11
Overall Yield: 27%

New Fragment B
11 Steps Linear

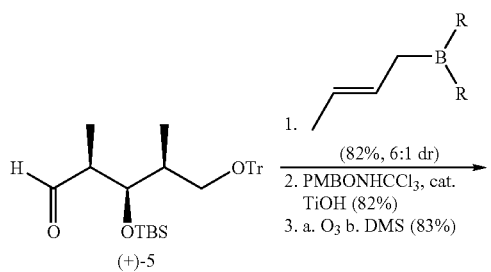

1. (crotylboration reagent) (82%, 6:1 dr)
2. PMBONHCCl₃, cat. TfOH (82%)
3. a. O₃ b. DMS (83%)

(+)-5

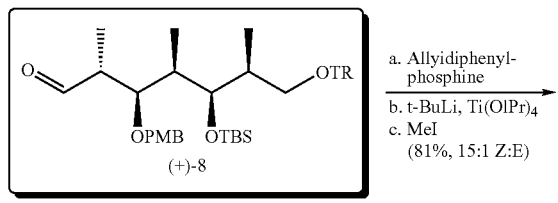

a. Allyldiphenyl-phosphine
b. t-BuLi, Ti(OiPr)₄
c. MeI
(81%, 15:1 Z:E)

(+)-8

Fragment C

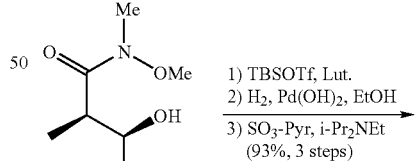

1) TBSOTf, Lut.
2) H₂, Pd(OH)₂, EtOH
3) SO₃-Pyr, i-Pr₂NEt
(93%, 3 steps)

(-)-CP

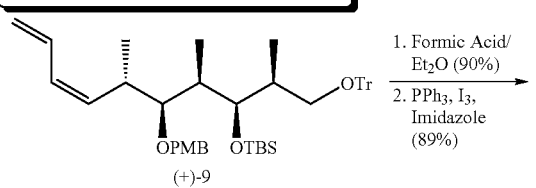

1. Formic Acid/Et₂O (90%)
2. PPh₃, I₃, Imidazole (89%)

(+)-9

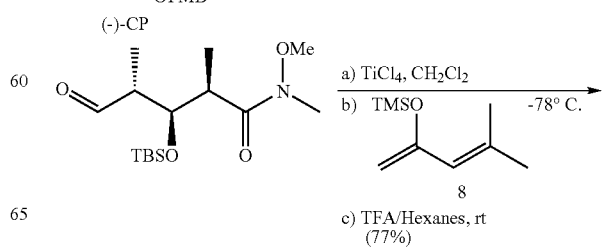

a) TiCl₄, CH₂Cl₂ -78° C.
b) TMSO (diene 8)
c) TFA/Hexanes, rt (77%)

(+)-A
13 Steps Linear

Total Steps: 13
Overall Yield: 19%

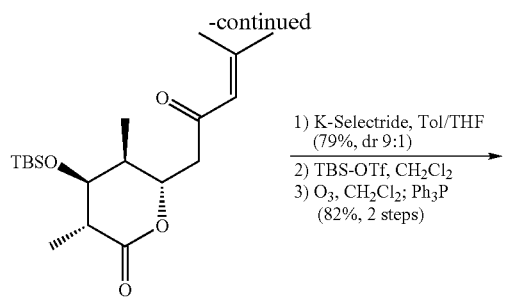
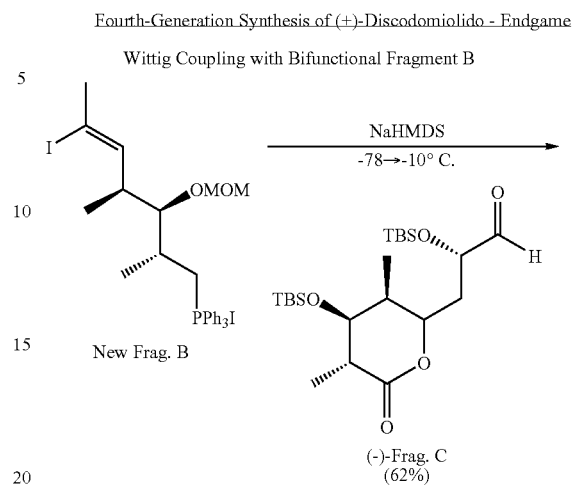
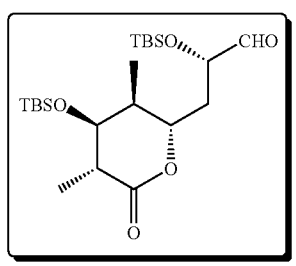
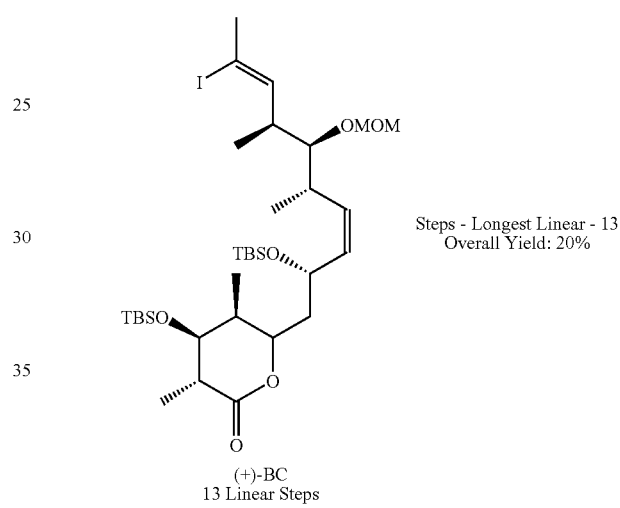
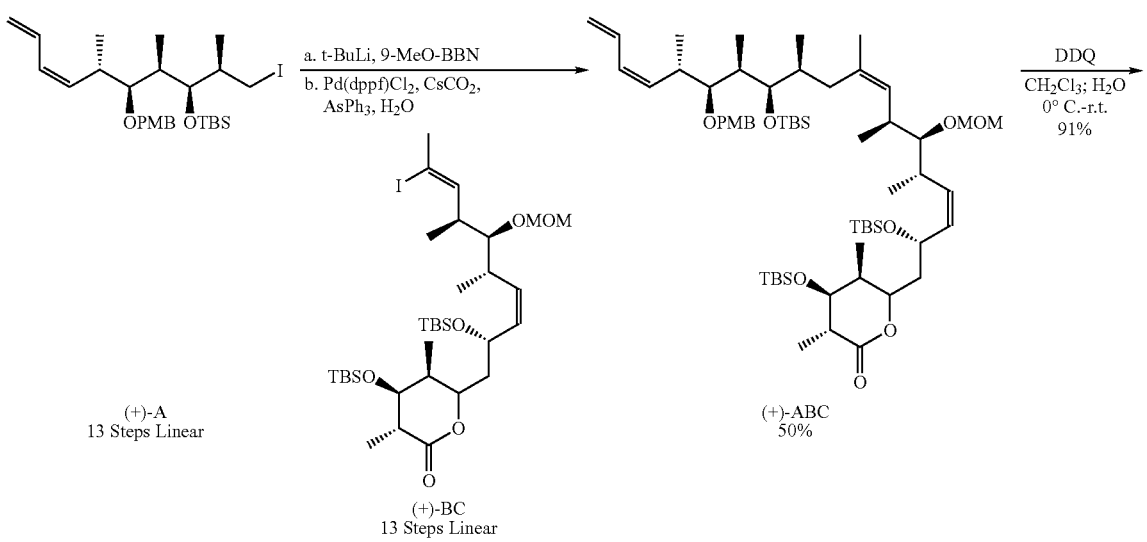

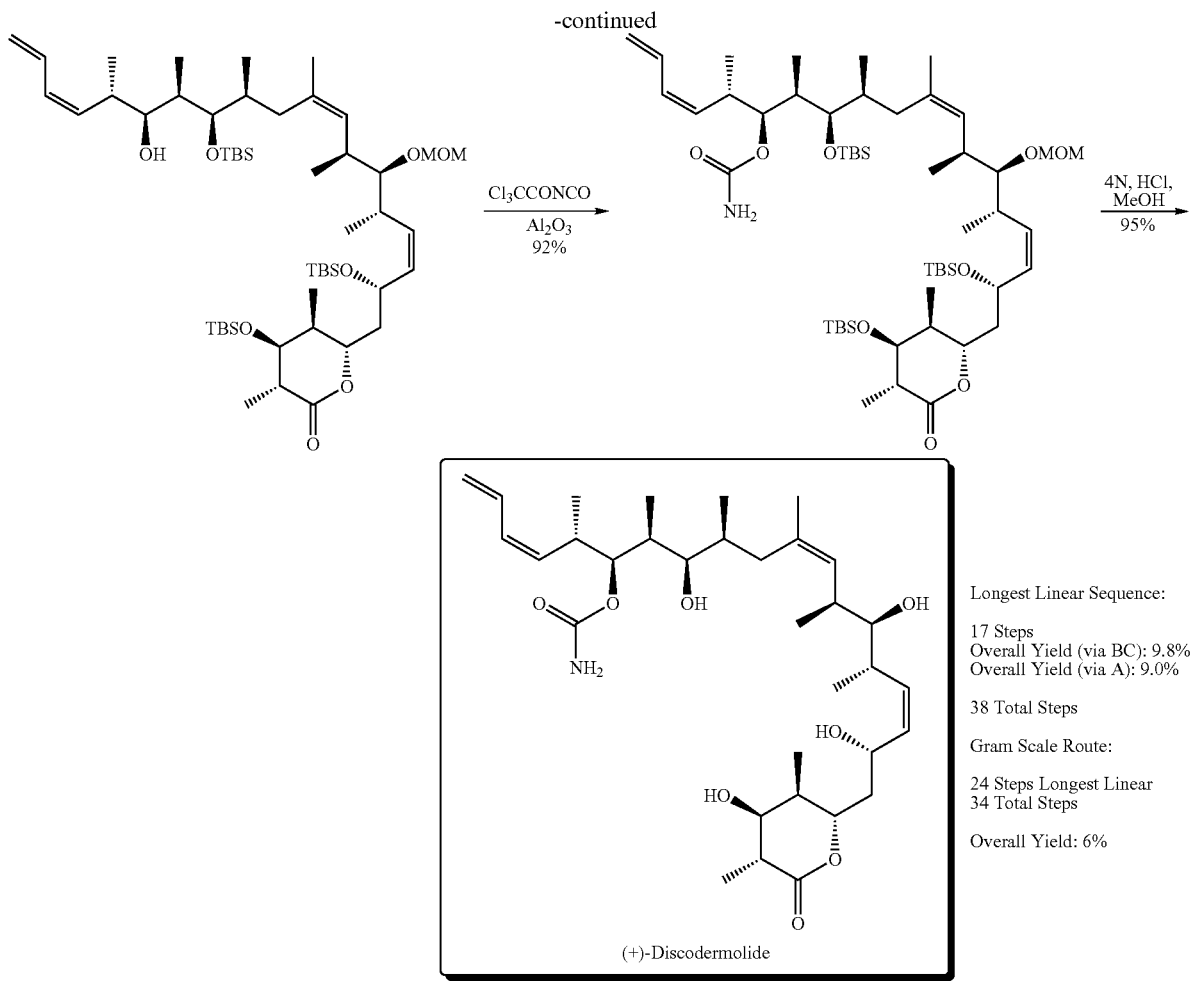
Additionally, the present invention also provides methods for adding a carbamoyl moiety to compounds of Formula I and III, yielding compounds of Formula II and IV, respectively. In particular, Schemes 5a, 5b and 6 show methods of synthesis to incorporate a carbamoyl moiety to the compound (+)-ABC, which ultimately results in the formation of (+)-discodermolide.
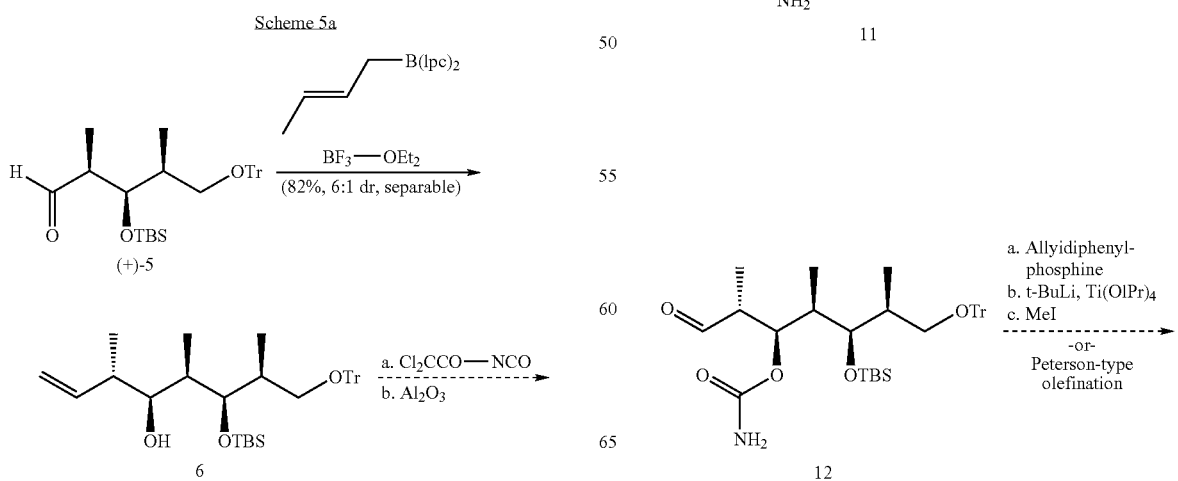

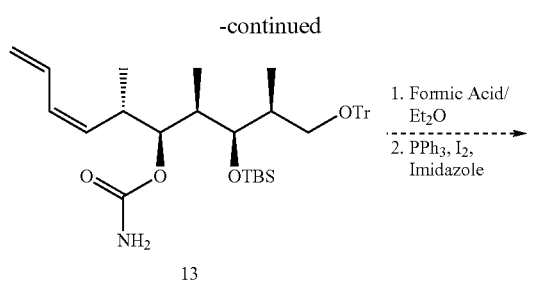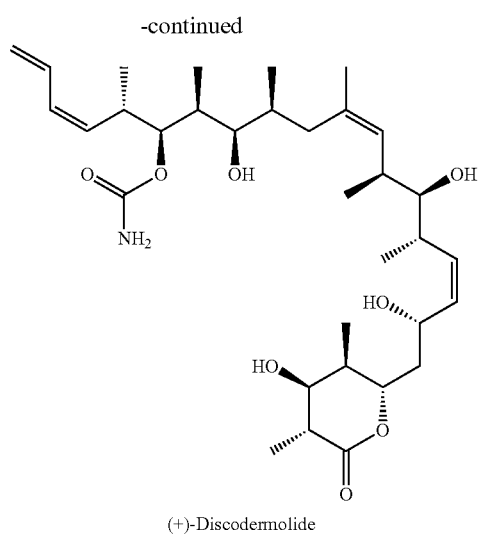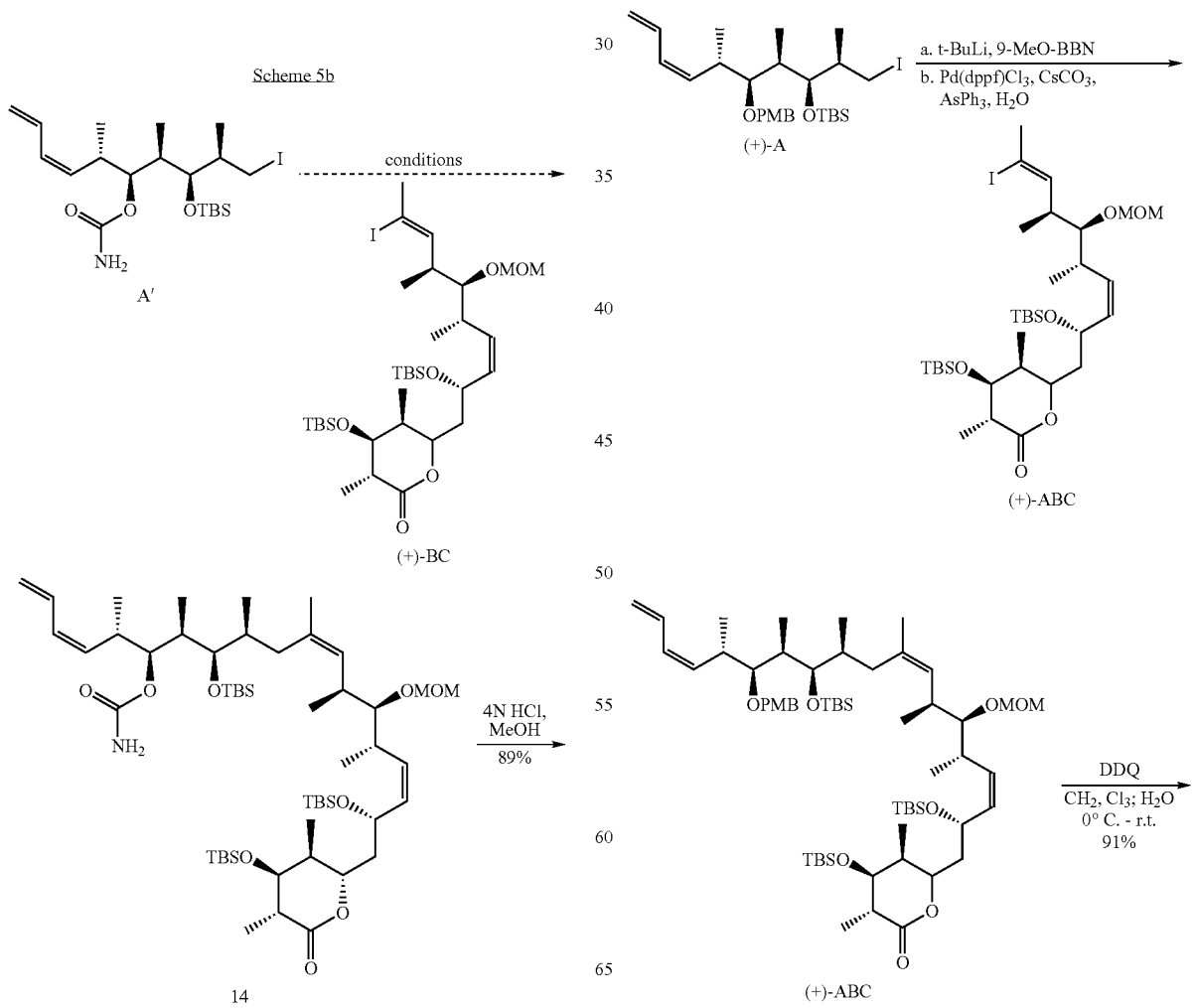

41

-continued

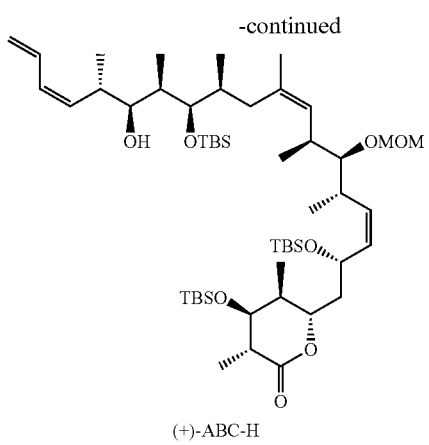

(+)-ABC-H

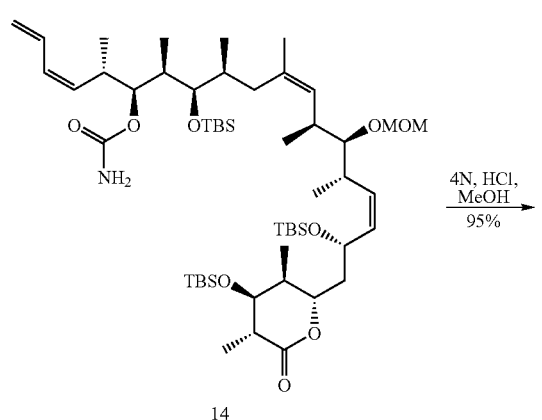

14

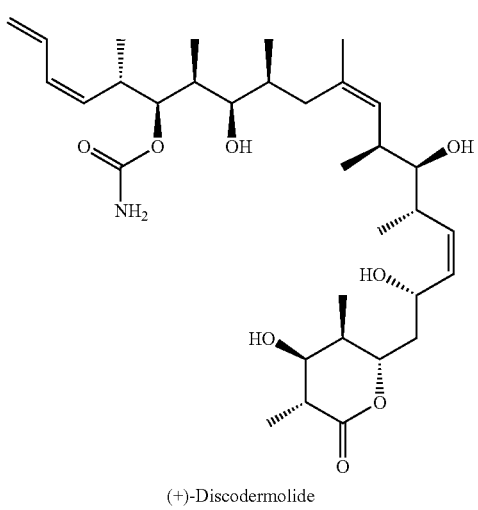

(+)-Discodermolide

42

EXAMPLES

The following examples provide reactions for forming the intermediates and final products described in Schemes 4a and 4b.

Example 1

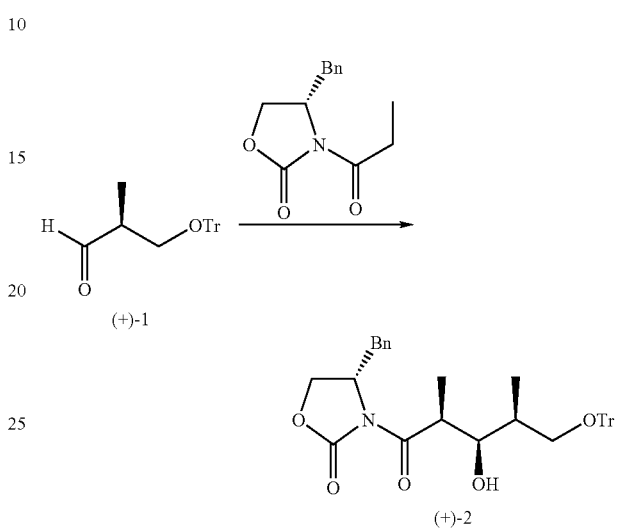

Alcohol (+)-2: A solution of oxazolidinone (+)-1a (1.79 g, 7.67 mmol) In degassed $CH_2Cl_2$ (30 mL, 4 Å MS dried, argon sparged) was cooled to 0° C. and n-$Bu_2$BOTf (1.0 M in hexane, 7.67 mL) was introduced, followed by addition of Ni$Pr_2$Et (1.34 mL, 8.05 mmol). The mixture was cooled to −78° C. A precooled (−78° C., degassed solution of aldehyde (+)-1 (2.2 g, 6.66 mmol) in $CH_2Cl_2$ (8 mL) was then added via cannula over 0.25 h (2 mL rinse). After an additional 1.0 h at −78° C., the reaction was warmed to −0° C., stirred for 1 h, then quenched with pH 7 potassium phosphate monobasic-sodium hydroxide buffer (0.05 M, 5.5 mL). A solution of 30% $H_2O_2$ in MeOH (1:2, 17 mL) was added to the vigorously stirred reaction mixture at such a rate as to maintain an internal temp <8° C. (15 min, 0° C. cooling bath). The reaction was stirred 1 h at room temperature, and the resulting layers were separated. The aqueous layer was extracted (3×$CH_2Cl_2$), and the combined organic layers were washed with saturated aqueous $NaHCO_3$ (15 mL), water (15 mL) and saturated brine (2×10 mL). The organic layer was dried over $MgSO_4$, filtered, and concentrated in vacuo. Flash chromatography (20% ethyl acetate/hexanes) provided (+)-2 (3.4 g, 85%) as a white foam. $[\alpha]_D^{23}$ +17.0° (c=1, $CHCl_3$); IR (NaCl) 3523, 3081, 3052, 2971, 2925, 2872, 1780, 1699, 1489, 1447, 1157, 1099, 1070; $^1$H NMR (500 MHz, $CDCl_3$) δ 7.48 (m, 6H), 7.37-7.29 (m, 8H), 7.28-7.20 (m, 6H), 4.67 (dddd, J=8.9, 5.6, 5.2, 3.7 Hz, 1H), 4.17 (d, J=5.2 Hz, 2H), 4.04 (ddd, J=5.9, 4.8, 3.3 Hz, 1H), 3.92 (dddd, J=6.7, 6.7, 6.7, 6.7 Hz, 1H), 3.25 (dd, J=13.4, 3.4 Hz, 1H), 3.23 (dd, J=9.3, 5.6 Hz, 1H), 3.17 (dd, J=9.3, 5.2 Hz, 1H), 2.96 (d, J=3.35 Hz, 1H), 2.78 (dd, J=13.4, 9.7 Hz, 1H), 1.89 (m, 1H), 1.32 (d, J=6.7 Hz, 3H), 1.09 (d, J=6.7 Hz, 3H); $^{13}$C NMR (125 MHz, $CDCl_3$) δ 176.8, 152.6, 143.9, 135.1, 129.4, 128.9, 128.6, 127.8, 127.4, 126.9, 86.9, 73.8, 67.0, 66.0, 55.1, 40.8, 37.7, 36.5, 13.2, 12.2; high resolution mass spectrum (ES+) m/z 586.2561, [(M)+, calcd for $C_{38}H_{37}NO_5Na$: 586.2569].

Example 2

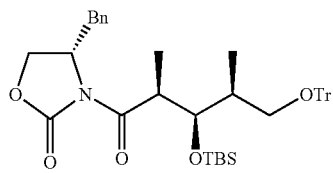

TBS Ether 3: A solution of alcohol (+)-2 (2.0 g, 3.55 mmol) and 2,6-lutidine (0.744 mL, 6.39 mmol) in $CH_2Cl_2$ (10 mL) was cooled to −30° C. and TBSOTf (1.15 mL, 4.97 mmol) was added over 3 min. After an additional 3 h at 0° C., the mixture was diluted with ether (100 mL), washed [aqueous $NaHSO_4$ (1.0 M) and brine (200 mL each)], dried over $MgSO_4$, filtered and concentrated. Flash chromatography (8% ethyl acetate/hexanes) afforded 3 (2.18 g, 80% yield) as a colorless oil. $[\alpha]_D^{23}$ +11.3° (c=1, $CHCl_3$); IR (NaCl) 3081, 3060, 3029, 2928, 2855, 1782, 1696, 1596, 1490, 1472, 1448, 1382, 1350, 1251, 1210, 1152, 1116, 1064, 868, 837, 762, 700; $^1H$ NMR (500 MHz, $CDCl_3$) δ 7.46-7.43 (m, 6H), 7.36-7.26 (m, 8H), 7.24-7.20 (m, 6H), 4.68-4.62 (m, 1H), 4.17 (App d, J=5.2 Hz, 2H), 4.07 (dd, J=7.4, 2.6 Hz, 1H), 3.94 (dddd, J=6.7, 6.7, 6.7, 6.7 Hz, 1H), 3.26 (dd, J=13.4, 3.4 Hz, 1H), 3.11 (dd, J=8.6, 5.6 Hz, 1H), 2.97 (dd, J=8.6, 8.6 Hz, 1H), 2.77 (dd, J=13.4, 9.7 Hz, 1H), 1.93 (m, 1H), 1.21 (d, J=6.7 Hz, 3H), 0.97 (d, J=6.7 Hz, 3H), 0.79 (s, 9H), −0.1 (s, 3H), −0.2 (s, 3H); $^{13}C$ NMR (125 MHz, $CDCl_3$) δ 175.8, 152.7, 135.3, 129.4, 128.9, 128.7, 127.9, 127.6, 127.3, 126.8, 86.5, 73.7, 66.7, 65.9, 55.4, 41.9, 39.5, 37.7, 25.9, 18.2, 14.9, 11.9, −3.9, −4.2; high resolution mass spectrum (ES+) m/z 700.3445, [(M)+, calcd for $C_{42}H_{51}NO_5SiNa$: 700.3434].

Example 3

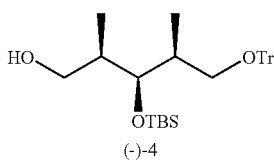

Alcohol (−)-4: At −30° C., a solution of TBS ether (+)-3 (1.70 g, 2.51 mmol) in THF (20 mL) was treated with EtOH (0.290 mL, 5.02 mmol). $LiBH_4$ (2.0 M in THF, 2.51 mL, 5.02 mmol) was added over 15 min. After an additional 1 h at 0° C. and 12 h at room temperature, the mixture was diluted with ether (30 mL), quenched carefully with aqueous NaOH (1.0 N, 9.6 mL), and stirred at room temperature for 4 h. Saturated $NH_4Cl$ solution (10 ml) was added, the layers were separated, and the aqueous layer was extracted with $Et_2O$ (3×20 mL). The combined organic layers were washed with brine (50 mL), dried over $Na_2SO_4$, filtered and concentrated. Flash chromatography (8% ethyl acetate/hexanes) provided (−)-4 (1.0 g, 80% yield) as a colorless oil. $[\alpha]_D^{23}$ −6.9° (c=1, $CHCl_3$); IR (NaCl) 3424, 3058, 3031, 2955, 2927, 2882, 2855, 1489, 1472, 1448, 1387, 1252, 1101, 1031, 836, 772, 705; $^1H$ NMR (500 MHz, $CDCl_3$) δ 7.45-7-42 (m, 6H), 7.32-7.26 (m, 6H), 7.24-7.21 (m, 3H), 3.87 (dd, J=3.35, 3.35 Hz, 1H), 3.64 (ddd, J=10.8, 8.6, 1.9 Hz, 1H), 3.46 (ddd, J=10.8, 5.6, 5.6 Hz, 1H), 3.00 (dd, J=8.9, 7.1 Hz, 1H), 2.77 (dd, J=8.9, 7.1 Hz, 1H), 2.15 (br s, 1H), 2.01 (dddd, J=7.1, 7.1, 7.1, 3.5 Hz, 1H), 1.89 (m, 1H), 0.98 (d, J=6.7 Hz, 3H), 0.82 (d, J=7.1 Hz, 3H), 0.81 (s, 9H), −0.01 (s, 3H), −0.2 (s, 3H); $^{13}C$ NMR (125 MHz, $CDCl_3$) δ 144.3, 128.7, 127.7, 126.8, 86.4, 74.8, 66.8, 66.2, 40.3, 36.3, 25.9, 18.1, 13.2, 12.8, −4.4, −4.5; high resolution mass spectrum (ES+) m/z 527.2970, [(M)+, calcd for $C_{32}H_{44}O_3SiNa$: 527.2957].

Example 4

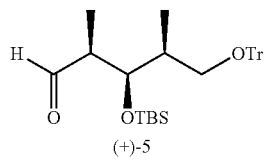

Aldehyde (+)-5: To a solution of alcohol (−)-4 (1.65 g, 3.81 mmol) in DMSO (4.0 mL) and $CH_2Cl_2$ (10 mL) at 0° C. was added $NEt_3$ (2.67 mL, 19.05 mmol) followed by $SO_3$·pyr (1.06 g, 6.8 mmol) in three portions over 20 minutes. Warmed to room temperature, stirred for 3 h, and then diluted with $CH_2Cl_2$ (50 mL) and $H_2O$ (10 mL). The layers were separated and the aqueous layer extracted with $CH_2Cl_2$ (1×15 mL); the combined organic layers were washed with $H_2O$ (2×10 mL), and brine (1×15 mL), dried over $MgSO_4$, filtered and concentrated in vacuo. The residue was then diluted with $C_6H_6$ (20 mL) and treated with $Na_2SO_4$, filtered, and concentrated in vacuo to afford the aldehyde (+)-5 (1.53 g, 93% yield), as a clear oil which slowly solidified on standing and which was routinely used without further purification. $[\alpha]_D^{23}$ +11.0° (c=1, $CHCl_3$); IR (NaCl) 3058, 3031, 2955, 2931, 2882, 2860, 1723, 1485, 1443, 1384, 1255, 1102, 1067, 1026, 832, 773, 702; $^1H$ NMR (500 MHz, $CDCl_3$) δ 9.78 (d, J=0.74 Hz, 1H), 7.44-7.41 (m, 6H), 7.32-7.29 (m, 6H), 7.25-7.21 (m, 3H), 4.19 (dd, J=4.5, 4.5 Hz, 1H), 3.06 (dd, J=8.9, 6.3 Hz, 1H), 2.99 (dd, J=8.9, 6.3 Hz, 1H), 2.44-2.38 (m, 1H), 1.90 (ddd, J=6.7, 6.7, 4.5 Hz, 1H), 0.98 (d, J=6.7 Hz, 3H), 0.92 (d, J=6.7 Hz, 3H), 0.80 (s, 9H), −0.02 (s, 3H), −0.11 (s, 3H); $^{13}C$ NMR (125 MHz, $CDCl_3$) δ 205.1, 144.1, 128.7, 127.7, 126.9, 86.6, 72.8, 66.2, 51.3, 37.7, 25.8, 18.1, 12.7, 8.9, −4.2, −4.6; high resolution mass spectrum (ES+) m/z 525.2804, [(M)+, calcd for $C_{32}H_{42}O_3SiNa$: 525.2801].

Example 5

6

Alcohol 6: The (0.530 g) was heated at 100° C. under high vac overnight to dry. The flask containing the potassium tert-butoxide was then charged with THF (16 mL) and cooled to −78° C. trans-2-butene (0.640 mL, excess) was then added via cannula, followed by the nBuLi (1.85 mL, 2.5 M in hexanes, 1.45 equiv.) dropwise over 20 min. to produce an orange suspension. Warmed to −50° C., and stirred for 0.5 h. The reaction was then cooled to −78° C. and treated with a precooled solution of (−)-methoxydiisocampheylborane (1.85 g, 1.7 equiv.) in 6 mL THF dropwise over 15 min. After an additional 30 min., the colorless slurry was treated with the BF$_3$*OEt$_2$ (0.804 mL, 2.0 equiv.) dropwise over 5 min., and a precooled solution of the aldehyde (+)-5 (1.60 g, 3.18 mmole) in THF (2.5 mL+0.5 ml rinse) via syringe over 0.5 h. After stirring for an additional 7 h, the pale yellow slurry was charged with the 3N NaOH (6 mL) and allowed to slowly warm to ambient temperature. During this period, H$_2$O$_2$ (30% aq., 6 mL) was added slowly to control evolution of gas after which the mixture heated to 60° C. for 4 h. The biphasic solution was then cooled to ambient temperature, and diluted with EtOAc (50 mL) and H$_2$O (10 mL). The aqueous phase was then extracted with EtOAc (2×50 mL) and the combined organic layers were washed with water (2×20 mL) and brine (1×50 mL), dried over MgSO$_4$, and concentrated in vacuo. Distillation of the ipc alcohol (bp ~60° C., 0.15 mmHg) and flash chromatography (2%-3% ethyl acetate/hexanes) afforded 1.25 g of alcohol 6 as a pale yellow oil in addition to 0.209 g of the undesired diastereomer for overall yield of 82%. [α]$_D^{23}$ −8.4° (c=2, CHCl$_3$); IR (NaCl) 3582, 3059, 3022, 2957, 2928, 2882, 2855, 1637, 1597, 1490, 1461, 1448, 1388, 1251, 1065, 1033, 1002, 921, 836, 772, 706; $^1$H NMR (500 MHz, CDCl$_3$) δ 7.47-7-43 (m, 6H), 7.32-7.27 (m, 6H), 7.25-7.21 (m, 3H), 5.77-5.69 (m, 1H), 5.14 (dd, J=7.1, 1.86 Hz, 1H), 5.11 (s, 1H), 3.76 (dd, J=6.33, 2.23 Hz, 1H), 3.32 (ddd, J=8.6, 3.0, 3.0 Hz, 1H), 3.10-3.00 (m, 2H), 2.31-2.21 (m, 1H), 2.08 (dddd, J=6.7, 6.7, 6.7, 2.2 Hz, 1H), 2.08 (dddd, J=7.1, 7.1, 7.1, 3.0 Hz, 1H), 1.62 (d, J=3.0, 1H), 0.975 (d, J=7.1 Hz, 3H), 0.965 (d, J=6.7 Hz, 3H), 0.86 (d, J=6.7 Hz, 3H), 0.79 (s, 9H), 0.00 (s, 3H), −0.24 (s, 3H); $^{13}$C NMR (125 MHz, CDCl$_3$) δ 144.4, 141.4, 128.7, 127.7, 126.8, 116.3, 86.4, 75.3, 74.9, 67.2, 42.5, 38.3, 37.6, 26.1, 18.3, 16.6, 11.9, 9.2, −3.8, −4.0; high resolution mass spectrum (CI) m/z 581.3426, [(M)$^+$, calcd for C$_{36}$H$_{50}$O$_3$SiNa: 581.3427].

Example 6

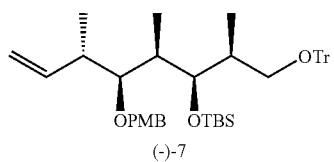

(−)-7

PMB Ether (−)-7. To a solution of alcohol 6 (0.102 g, 0.182 mmol) in methylene chloride (2.0 mL) at −30 was added PMB-trichloroacetimidate (0.050 g, 0.182 mmol) followed by trifluoromethanesulfonic acid as a 0.5M solution in CH$_2$Cl$_2$ (0.050 mL, 0.025 mmol). The solution slowly warmed to −10° C. and stirred 1 h, after which additional PMB-trichloroacetimidate (0.050 g, 0.182 mmol) was added. The reaction mixture stirred for an additional 1 h at −10° C. and quenched with NH$_4$Cl (1 mL) and extracted with methylene chloride (3×10 mL). The combined organic layers were washed 2×5 mL H$_2$O, 1×5 mL brine, and dried (Na$_2$SO$_4$), and concentrated in vacuo. Flash chromatography (ethyl acetate/hexane, 2%) gave 0.100 g (82% yield) of (−)-7. [α]$_D^{23}$ −6.1° (c=1, CHCl$_3$); IR (NaCl) 3059, 2956, 2928, 2882, 2855, 1613, 1513, 1490, 1462, 1448, 1248, 1172, 1061, 1036, 912, 836, 767, 702, 743, 632; $^1$H NMR (500 MHz, CDCl$_3$) δ 7.45-7-40 (m, 6H), 7.27-7.24 (m, 6H), 7.22-7.17 (m, 5H), 6.85-6.79 (m, 2H), 5.87 (ddd, J=17.5, 10.4, 8.2 Hz, 1H), 5.01-4.94 (m, 2H), 4.50 (d, J=10.8 Hz, 1H), 4.39 (d, J=10.8 Hz, 1H), 3.79 (s, 3H), 3.62 (dd, J=5.6, 3.0 Hz, 1H), 3.18 (dd, J=5.2, 5.2 Hz, 1H), 3.08 (dd, J=8.9, 5.6 Hz, 1H), 2.91 (dd, J=8.6, 8.6 Hz, 1H), 2.50-2.43 (m, 1H), 2.07-1.98 (m, 1H), 1.76 (ddddd, J=7.1, 7.1, 6.0, 6.0, 6.0 Hz, 1H), 1.05 (d, J=6.7 Hz, 3H), 0.94 (d, J=7.1 Hz, 3H), 0.88 (d, J=7.1 Hz, 3H), 0.79 (s, 9H), −0.03 (s, 3H), −0.23 (s, 3H); $^{13}$C NMR (125 MHz, CDCl$_3$) δ 158.9, 144.4, 141.1, 131.2, 128.9, 128.7, 127.6, 126.8, 114.6, 113.6, 86.5, 84.1, 74.4, 73.7, 67.1, 55.2, 41.4, 39.9, 38.7, 26.1, 18.4, 17.6, 12.2, 10.9, −3.6, −4.0; high resolution mass spectrum (ES+) m/z 701.3982, [(M)$^+$, calcd for C$_{44}$H$_{58}$O$_4$SiNa: 701.40021].

Example 7

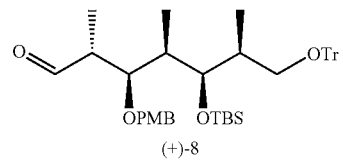

(+)-8

Aldehyde (+)-8: A solution of the olefin (−)-7 (70 mg, 0.103 mmole), pyridine (0.100 mL), and a catalytic amount of Sudan III in CH$_2$Cl$_2$:MeOH (0.9 mL:0.9 mL) was cooled to −78° C. and a stream of ozone was bubbled through the orangish/pink solution for 3 min. until a yellowish/brown color persisted. The reaction was immediately purged with a stream of argon, and treated with dimethylsulfide (0.330 mL, 4.5 mmole). and the solution was allowed to slowly warm to ambient temperature. After 4 h, the orange solution was diluted with Et$_2$O, washed with CuSO$_4$ (3×5 mL) and brine (1×5 mL), and dried over MgSO$_4$. Concentration in vacuo and purification via flash chromatography (ethyl acetate/hexane, 3%) gave 58 mg (83% yield) of (+)-8 as a slightly orange oil. $^1$HNMR (500 MHz, C$_6$D$_6$) δ 9.77 (d, J=2.1 Hz, 1H), 7.63 (apparent d, J=8.5 Hz, 6H), 7.24 (apparent d, J=8.6 Hz, 2H), 7.18 (m, 6H), 7.07 (apparent t, J=7.3 Hz, 3H), 6.82 (d, J=8.7 Hz, 2H), 4.49 (dd, J=14.5, 10.8 Hz, 2H), 3.95 (dd, J=6.7, 1.8 Hz, 1H), 3.64 (dd, J=6.3, 3.7 Hz, 1H), 3.36 (m, 1H), 3.35 (s, 3H), 3.28 (dd, J=8.9, 7.4 Hz, 1H), 2.63 (m, 1H), 2.24 (m, 1H), 1.93 (m, 1H), 1.12 (d, J=7.0 Hz, 3H), 1.09 (d, J=6.9 Hz, 3H), 0.96 (s, 9H), 0.92 (d, J=6.9 Hz, 3H), 0.09 (s, 3H), 0.08 (s, 3H); $^{13}$CNMR (125 MHz, C$_6$D$_6$) δ 202.5, 159.5, 144.6, 130.6, 128.9, 127.4, 127.3, 127.0, 113.8, 87.0, 81.9, 74.2, 73.7, 67.4, 54.4, 49.5, 40.6, 38.3, 26.1, 18.3, 11.6, 11.5, 11.3, −3.6, −4.1; high resolution mass spectrum (ES$^+$) m/z 703.3816 [(M+Na)$^+$; calcd for C$_{43}$H$_{56}$O$_5$SiNa: 703.3795.

Example 8

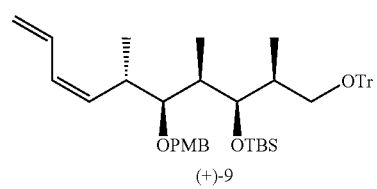

(+)-9

Diene (+)-9: To a −78° C. solution of freshly distilled allyldiphenylphosphine (1.11 mL, 5.14 mmol) in THF (15 mL, degassed) was added 3.0 mL of t-butyllithium (1.7 M in pentane, 5.14 mmol) and stirred for 5 min. The solution was warmed to 0° C., stirred for 30 min and cooled to −78° C. The solution was treated with freshly distilled Ti(Oi-Pr)$_4$ (1.52 mL, 5.14 mmol) and stirred for 30 min. A precooled (−78° C.) solution of aldehyde (+)-8 (1.75 g, 2.57 mmol) in THF (10 mL) was added via cannula (rinse 1×2 mL) and stirred for 1 h, then warmed to 0° C. Iodomethane (1.6 mL, 25.7 mmol) was added, and the solution was warmed to ambient temperature and stirred for 16 h. The solution was quenched with pH 7.0 buffer (25 mL) and extracted with CH$_2$Cl$_2$ (3×) and Et$_2$O (3×). The combined organic layers were washed with saturated brine solution, dried (MgSO$_4$), filtered and concentrated. Flash chromatography (2% EtOAc/hexanes) provided trityl protected diene (+)-9 (1.47 g, 81%, dr 16:1). [α]$_D^{23}$ +17.1 (c 0.35, CHCl$_3$; IR 3058, 2960, 2928, 2855, 1616, 1515, 1258 cm$^{-1}$; $^1$HNMR (500 MHz, C$_6$D$_6$) δ 7.65 (d, J=7.3 Hz, 6H), 7.33 (d, J=8.5 Hz, 2H), 7.20 (m, 6H), 7.08 (apparent t, J=7.3 Hz, 3H), 6.85 (d, J=8.6 Hz, 2H), 6.75 (ddd, J=16.8, 10.7, 10.7 Hz, 1H), 6.04 (t, J=11 Hz, 1H), 5.61 (t, J=10.4 Hz, 1H), 5.15 (d, J=16.8 Hz, 1H), 5.06 (d, J=10.1 Hz, 1H), 4.64 (d, J=10.6 Hz, 1H), 4.53 (d, J=10.6 Hz, 1H), 3.85 (dd, J=6.1, 2.9 Hz, 1H), 3.36 (s, 3H), 3.44-3.36 (m, 2H), 3.25 (t, J=8.5 Hz, 1H), 3.14 (m, 1H), 2.02 (m, 1H), 1.27 (d, J=6.8 Hz, 3H), 1.25 (d, J=6.9 Hz, 3H), 1.13 (d, J=6.8 Hz, 3H), 1.02 (s, 9H), 0.16 (s, 3H), −0.02 (s, 3H); $^{13}$CNMR (125 MHz, C$_6$D$_6$) δ 159.4, 144.7, 135.1, 132.6, 131.3, 129.4, 129.2, 129.0, 127.4, 126.9, 117.3, 113.8, 86.9, 84.3, 74.7, 74.2, 67.4, 54.5, 40.2, 39.0, 35.9, 26.3, 18.5, 18.3, 12.3, 11.3, −3.5, −4.0; high resolution mass spectrum (ES$^+$) m/z 727.4174 [(M+Na)$^+$; calcd for C$_{46}$H$_{60}$O$_4$SiNa: 727.4159.

Example 9

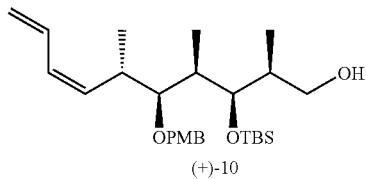

(+)-10

Diene alcohol (+)-10: To a solution of diene (+)-9 (1.30 g, 2.27 mmol) in diethyl ether (42 mL) at room temperature was added a 1:1 solution of formic acid in ether (42 mL:42 mL) dropwise. Stirred 3 h, diluted with water (30 mL), and quenched via careful addition of solid K$_2$CO$_3$. The layers were separated, the aqueous layer was extracted with Et$_2$O (3×30 mL), and the resulting organic layers were combined and concentrated in vacuo. The residue was dissolved In MeOH (60 mL), treated with K$_2$CO$_3$ (1.3 g) and stirred for 5 min. The resulting mixture was concentrated and subjected directly to flash chromatography (gradient elution: 10% to 15% EtOAc/hexanes) provided (+)-10 (0.978 g, 93% yield). [α]$_D^{23}$ +26.6 (c 1.4 CHCl$_3$); IR 3446, 2957, 2929, 2856, 1612, 1514, 1462, 1249, 1037 cm$^{-1}$; $^1$HNMR (500 MHz, CDCl$_3$) δ7.27 (d, J=8.6 Hz, 2H), 6.86 (d, J=8.6 Hz, 2H), 6.63 (ddd, J=16.6, 10.6, 10.6 Hz, 1H), 6.03 (apparent t, J=10.9 Hz, 1H), 5.57 (apparent, J=10.5 Hz, 1H), 5.21 (d, J=16.8 Hz, 1H), 5.12 (d, J=10.1 Hz, 1H), 4.55 (d, J=10.6 Hz, 1H), 4.46 (d, J=10.6 Hz, 1H), 3.80 (s, 3H), 3.71 (t, J=4.2 Hz, 1H), 3.54 (dd, J=7.2, 10.5 Hz, 1H), 3.41 (dd, J=6.2, 10.5 Hz, 1H), 3.23 (dd, J=4.5, 6.5 Hz, 1H), 2.99 (m, 1H), 1.84 (m, 2H), 1.59 (br s, 1H), 1.09 (d, J=6.8 Hz, 3H), 1.02 (d, J=6.9 Hz, 3H), 0.93 (s, 9H), 0.83 (d, J=6.9 Hz, 3H) 0.10 (s, 3H), 0.09 (s, 3H); $^{13}$CNMR (125 MHz, CDCl$_3$) δ 159.0, 137.2, 134.8, 132.3, 131.2, 129.2, 117.5, 113.6, 84.2, 74.7, 73.5, 65.9, 55.2, 40.5, 39.8, 35.6, 26.1, 18.6, 18.4, 12.1, 10.9, −3.7, −3.9; high resolution mass spectrum (ES$^+$) m/z 485.3052 [(M+Na)$^+$; calcd for C$_{27}$H$_{46}$O$_4$SiNa: 485.3063

Example 10

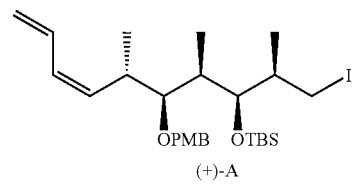

(+)-A (+)-A: A solution of iodine (0.64 g, 2.53 mmol) in 6 mL Et$_2$O was added dropwise to a vigorously stirred solution of diene alcohol (+)-10 (0.78 g, 1.69 mmol), PPh$_3$ (0.84 g, 3.21 mmol) and imidazole (0.22 g, 3.21 mmol) in benzene/ether (1:2, 30 mL) at 0° C. The resulting suspension was stirred 40 min at room temperature and poured into 300 mL of 1:1 water and ether. The layers were separated, the organic layer was washed with saturated NaS$_2$O$_3$ solution (2×), water (1×), 6% H$_2$O$_2$ (3×), brine (1×). The organic layer was dried over Na$_2$SO$_4$, filtered and concentrated. Flash chromatography (5% EtOAc/hexanes) provided the (+)-A as colorless oil (0.95 g, 98%). [α]$_D^{23}$ +44.0° (c=1, C$_6$H$_6$); IR (NaCl) 2958, 2930, 2886, 2856, 1612, 1513, 1462, 1373, 1300, 1249, 1172, 1039, 1006, 954, 903, 834, 773; $^1$H NMR (500 MHz, CDCl$_3$) δ727 (m, 2H), 6.86 (m, 2H), 6.62 (dddd, J=16.8, 11.2, 10.0, 1.1 Hz, 1H), 6.03 (dd, J=11.2, 1.1 Hz, 1H), 5.53 (dd t, J=10.0, 10.0 Hz, 1H), 5.20 (dd, J=16.8, 2.2 Hz, 1H), 5.12 (d, J=10.0 Hz, 1H), 4.57 (d, J=10.8 Hz, 1H), 4.47 (d, J=10.8 Hz, 1H), 3.81 (s, 3H), 3.60 (dd, J=5.2, 3.4 Hz, 1H), 3.22-3.17 (m, 2H), 2.99 (dd, J=9.3, 8.6 Hz, 1H), 2.99-2.94 (m, 1H), 1.84 (m, 1H), 1.77 (dddd, J=13.8, 6.7, 5.6, 5.6 Hz, 1H), 1.06 (d, J=7.1 Hz, 3H), 0.99 (d, J=7.1 Hz, 3H), 0.97 (d, J=6.7 Hz, 3H), 0.93 (s, 9H), 0.09 (app s, 6H); $^{13}$C NMR (125 MHz, CDCl$_3$) δ 159.0, 134.6, 132.4, 131.1, 129.3, 129.2, 117.6, 113.6, 83.8, 74.9, 74.5, 55.2, 41.7, 40.1, 35.6, 26.1, 18.6, 18.5, 15.2, 13.6, 11.1, −3.5, −3.7; high resolution mass spectrum (CI) m/z 595.2060, [(M)$^+$, calcd for C$_{27}$H$_{45}$IO$_3$SiNa: 595.2080].

Example 11

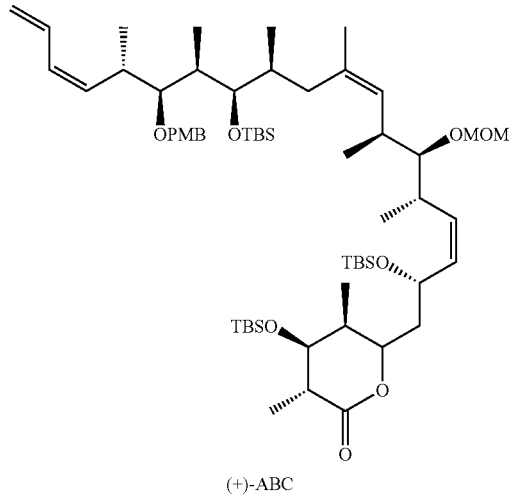

(+)-ABC

Tetraene (+)-ABC: A sample of (+)-A (180 mg, 0.314 mmol) was taken up in Et$_2$O (2 mL) and MeO-9-BBN (1M In hexanes, 0.376 mL, 0.376 mmol) was added. The resulting mixture was cooled to −78° C. and argon was bubbled through for 10 min. t-BuLi (1.7M in pentane, 0.360 mL, 0.612 mmol) was added dropwise via syringe, followed by THF (2 mL) and the resulting cloudy mixture warmed to room temperature and stirred for 1 h. The resulting mixture was then transferred via cannula to a flask containing DMF (2.0 ml), vinyl iodide (+)-BC (195 mg, 0.256 mmol), Pd(dppf)Cl$_2$ (21 mg, 10 mol %), AsPh$_3$ (27 mg, 30 mol %), and 0.240 mL CsCO$_3$ as a 3.0M solution in H$_2$O. The flask containing the resulting red/brown solution was covered with aluminum foil, and stirred at room temperature for 20 h. The reaction mixture was then diluted with H$_2$O (3 mL) and ether (10 mL), the layers separated, and the aqueous layer extracted with ether (3×10 mL). The combined organics were washed with brine (1×10 mL), dried over MgSO$_4$, and concentrated in vacuo. Flash chromatography with 3% ethyl acetate/hexane as eluent yields (+)-ABC (165 mg, 50% yield) with a small amount (~10%) of BBN related byproducts evident by NMR. This mixture could be taken directly into the subsequent reaction. An analytical sample was isolated via flash chromatography (1% to 2% ethyl acetate/hexanes as eluent) with a 200:1 mass to mass ratio of silica gel to sample. $[\alpha]_D^{23}$ 32.0° (c 0.3 CHCl$_3$); IR (NaCl) 2958, 2929, 2884, 2857, 1734, 1472, 1253, 1045, 836 cm$^{-1}$; $^1$H NMR (500 MHz, CDCl$_3$) δ 7.25 (d, J=8.1 Hz, 2H), 6.84 (d, J=8.9 Hz, 2H), 6.57 (ddd, J=17.1, 10.8, 10.8 Hz, 1H), 6.00 (apparent t, J=10.8 Hz, 1H), 5.55 (apparent t, J=10.8 Hz, 1H), 5.31 (dd, J=10.8, 7.8 Hz, 1H), 5.24-5.16 (m, 2H), 5.10 (d, J=10.4 Hz, 1H), 4.99 (d, J=10.0 Hz, 1H), 4.80 (apparent t, J=8.9 Hz, 1H), 4.59 (ABq, $J_{AB}$=6.7 Hz, $\Delta\nu_{AB}$=26.4 Hz, 2H), 4.54 (d, J=10.4 Hz, 2H), 4.19 (apparent t, J=10.8 Hz, 1H), 3.77 (s, 3H), 3.61 (apparent t, J=2.6 Hz, 1H), 3.43 (apparent t, J=4.1 Hz, 1H), 3.24 (s, 3H), 3.23 (dd, J=7.4, 3.7 Hz, 1H), 3.04 (apparent t, J=5.6 Hz, 1H), 2.98 (ddd, J=10.0, 6.7, 3.3 Hz, 1H), 2.73-2.65 (m, 1H), 2.60 (ddd, J=15.3, 7.4, 3.0 Hz, 1H), 2.49 (ddd, J=16.8, 13.0, 6.3 Hz, 1H), 2.02 (apparent t, J=12.3 Hz, 1H), 1.85-1.61 (m, 4H), 1.60-1.54 (m, 2H), 1.54 (s, 3H), 1.22 (d, J=7.4 Hz, 3H), 1.08 (d, J=6.7 Hz, 3H), 0.99 (d, J=7.1 Hz, 3H), 0.96-0.91 (m, 6H), 0.93 (s, 9H), 0.90 (d, J=6.7 Hz, 3H), 0.87 (s, 9H), 0.85 (s, 9H), 0.70 (d, J=7.1 Hz, 3H), 0.08 (s, 3H), 0.07 (s, 3H), 0.06 (s, 3H), 0.05 (s, 3H), 0.03 (br s, 6H, $^{13}$C NMR (125 MHz, CDCl$_3$) δ 173.3, 158.9, 134.4, 133.6, 132.4, 132.1, 131.9, 131.2, 130.8, 129.1, 129.0, 117.6, 113.6, 97.4, 86.3, 84.5, 77.0, 74.9, 74.69, 74.68, 64.6, 55.9, 55.2, 43.9, 42.3, 40.1, 36.2, 35.5, 35.3 (2), 34.2, 34.1, 26.2, 25.8, 25.6, 23.0, 18.6, 18.5, 18.0, 17.8, 16.63, 16.61, 16.2, 14.7, 13.9, 10.5, −3.29, −3.32, −4.4, −4.6, −4.9 (2); high resolution mass spectrum (ES+) m/z 1079.7214 [(M+Na)$^+$; calcd for C$_{60}$H$_{108}$O$_9$Si$_3$Na: 1079.7199].

What is claimed is:

1. A process for synthesizing a compound of formula I

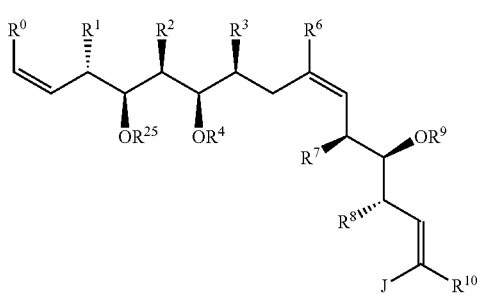

comprising contacting a compound of formula i

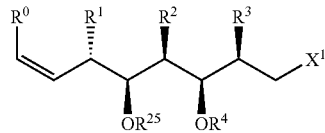

with a compound of formula xx

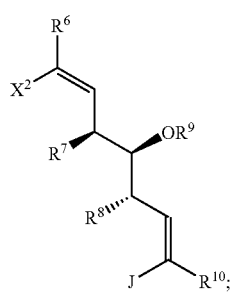

in the presence of a catalytically effective amount of a cross-coupling metal catalyst; wherein
R$^0$ is C$_{1-6}$ alkyl, C$_{2-6}$ alkenyl, C$_{2-6}$ alkynyl, (CH$_2$)$_r$(C$_{3-6}$ cycloalkyl), (CH$_2$)$_r$(aryl) or (CH$_2$)$_r$(heterocycle), wherein r is 0, 1, 2, 3, or 4;
R$^1$, R$^2$, and R$^3$ are, independently, H or C$_1$-C$_{10}$ alkyl;
R$^6$, R$^7$, and R$^8$ are, independently, C$_1$-C$_{10}$ alkyl;
R$^4$ and R$^9$ are, independently, H or an acid labile hydroxyl protecting group;
R$^{10}$ is hydrogen;
R$^{25}$ is hydrogen or an oxidation labile hydroxyl protecting group;
X$^1$ and X$^2$ are, independently, halogen; and
J is

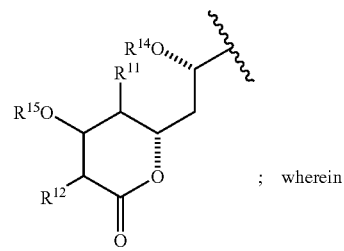

; wherein

R$^{11}$ and R$^{12}$ are each independently C$_1$-C$_{10}$ alkyl; and
R$^{14}$ and R$^{15}$ are, independently, H or an acid labile hydroxyl protecting group.

2. The process of claim 1, wherein the cross-coupling metal catalyst comprises nickel or palladium.

3. The process of claim 1, wherein the cross-coupling metal catalyst is Pd(0).

4. The process of claim 1, further comprising contacting the compound of formula i with a metallating agent, wherein the metallating agent is a compound containing boron, zinc, tin, magnesium, or aluminum, or a combination thereof.

5. The process of claim 4, wherein the metallating agent is a compound containing boron.

6. The process of claim 4, wherein the metallating agent is MeO-9-BBN.

7. The process of claim 4, wherein the metallating agent is a compound containing zinc.

8. The process of claim 4, wherein the metallating agent is $ZnCl_2$.

9. The process of claim 1, wherein $X^1$ and $X^2$ are iodo.

10. The process of claim 1, wherein $R^0$ is ethylenyl.

11. The process of claim 1, wherein $R^1$, $R^2$, $R^3$, $R^6$, $R^7$, and $R^8$ are, independently, $C_1$-$C_3$ alkyl.

12. The process of claim 1, wherein $R^1$, $R^2$, $R^3$, $R^6$, $R^7$, and $R^8$ are $CH_3$.

13. The process of claim 1, wherein $R^4$ and $R^9$, independently, are tert-butyldimethylsilyl, triethylsilyl, methoxymethyl, methylthiomethyl, 2-methoxyethoxymethyl, acetyl, benzyloxymethyl, 2-(trimethylsilyl)ethoxymethyl or allyl.

14. The process of claim 1, wherein $R^4$ is tert-butyldimethylsilyl.

15. The process of claim 1, wherein $R^9$ is methoxymethyl.

16. The process of claim 1, wherein $R^{10}$ is $CH_3$.

17. The process of claim 1, wherein $R^{11}$, $R^{12}$ and $R^{13}$ are $CH_3$.

18. The process of claim 1, wherein $R^{14}$ and $R^{15}$ are, independently, tert-butyldimethylsilyl, triethylsilyl, methoxymethyl, methylthiomethyl, 2-methoxyethoxymethyl, acetyl, benzyloxymethyl, 2-(trimethylsilyl)ethoxymethyl or allyl.

19. The process of claim 1, wherein $R^{14}$ and $R^{15}$ are, independently, tert-butyldimethylsilyl or methoxymethyl.

20. The process of claim 1, wherein $R^{25}$ is para-methoxybenzyl.

21. The process of claim 1, wherein J is

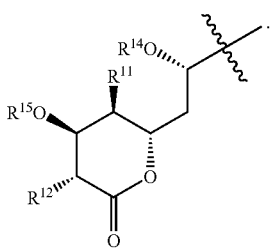

22. The process of claim 1, wherein J is

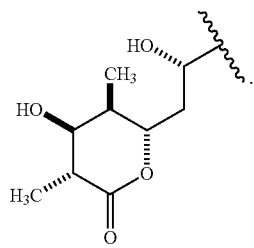

23. The process of claim 1, further comprising a step of synthesizing a compound of formula II

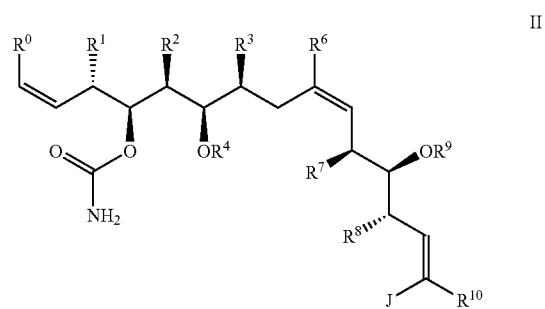

comprising
contacting the compound of formula I with an oxidizing agent to form a deprotected compound, and
contacting the deprotected compound with $Cl_3CCONCO$ and hydrolyzing the resultant imide to form the compound of formula II.

24. The process of claim 23, wherein the oxidizing agent is 2,3-dichloro-5,6-dicyano-1,4-benzoquinone.

25. The process of claim 23, wherein the hydrolysis of the imide is carried out in the presence of $Al_2O_3$.

* * * * *